United States Patent
Kim et al.

(10) Patent No.: US 9,080,155 B2
(45) Date of Patent: Jul. 14, 2015

(54) O-ACETYLHOMOSERINE SULFHYDRYLASE OR MUTANT PROTEIN THEREOF, AND METHOD FOR CONVERTING TO METHIONINE USING THE SAME

(75) Inventors: So Young Kim, Gyeonggi-do (KR); Yong Uk Shin, Gyeonggi-do (KR); Chang Il Seo, Incheon (KR); Sung Kwang Son, Seoul (KR); In Kyung Heo, Seoul (KR); Han Jin Lee, Seoul (KR); Ju Eun Kim, Seoul (KR); Hyun Ah Kim, Jeollabuk-do (KR); Jee Yeon Bae, Incheon (KR); Kwang Ho Na, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 13/997,054

(22) PCT Filed: Dec. 21, 2011

(86) PCT No.: PCT/KR2011/009965
§ 371 (c)(1),
(2), (4) Date: Jun. 21, 2013

(87) PCT Pub. No.: WO2012/087038
PCT Pub. Date: Jun. 28, 2012

(65) Prior Publication Data
US 2013/0273614 A1 Oct. 17, 2013

(30) Foreign Application Priority Data
Dec. 21, 2010 (KR) .................. 10-2010-0131954

(51) Int. Cl.
*C12N 9/10* (2006.01)
*C12P 7/54* (2006.01)
*C12P 13/12* (2006.01)

(52) U.S. Cl.
CPC .............. *C12N 9/1085* (2013.01); *C12P 7/54* (2013.01); *C12P 13/12* (2013.01); *C12Y 205/01049* (2013.01)

(58) Field of Classification Search
None
See application file for complete search history.

(56) References Cited

U.S. PATENT DOCUMENTS 7,611,873 B1 11/2009 Usuda et al.
7,662,943 B2 2/2010 Park et al.
(Continued)

FOREIGN PATENT DOCUMENTS

JP 2009-544309 A 12/2009
WO 2004/108894 A2 12/2004
WO WO 2008013432 A1 * 1/2008

OTHER PUBLICATIONS

GenBank Accession No. YP_002524520.1, available 2009.*
(Continued)

*Primary Examiner* — Rebecca Prouty
*Assistant Examiner* — Richard Ekstrom
(74) *Attorney, Agent, or Firm* — Seed IP Law Group PLLC

(57) ABSTRACT

The present invention relates to a novel protein having O-acetylhomoserine sulfhydrylase activity, a mutant protein thereof, a polynucleotide encoding the same, a recombinant vector comprising the polynucleotide, a microorganism transformed with the recombinant vector, and a method for producing methionine or acetic acid using the protein. The production method of the present invention has the advantage of producing L-methionine and acetic acid cost-effectively through having higher conversion rate and reduced reaction time compared to the existing methods, and it can minimize the amount of enzyme homogenate added when using the mutant protein, thereby easily producing L-methionine and acetic acid at high yield.

12 Claims, 5 Drawing Sheets

(56) References Cited

U.S. PATENT DOCUMENTS

| | | |
|---|---|---|
| 7,851,180 B2 | 12/2010 | Shin et al. |
| 8,426,171 B2 | 4/2013 | Kim et al. |
| 2010/0184164 A1 | 7/2010 | Kim et al. |
| 2012/0123158 A1 | 5/2012 | Kim et al. |

OTHER PUBLICATIONS

GenBank Accession No. EEW25407.1, published 2009.*
GenBank Accession No. EBA03892.1, published 2007.*
GenBank Accession No. YP_509796.1, available 2007.*
Chen et al., "Silencing of episomal transgene expression by plasmid bacterial DNA elements in vivo," *Gene Therapy* 11:856-864, 2004.
Ehrhardt et al., "Optimization of Cis-Acting Elements for Gene Expression from Nonviral Vectors In Vivo," *Human Gene Therapy* 14:215-225, Feb. 10, 2003.
Izsvák et al., "*Sleeping Beauty*, a Wide Host-range Transposon Vector for Genetic Transformation in Vertebrates," *J. Mol. Biol.* 302:93-102, 2000.
Yew et al., "CpG-Depleted Plasmid DNA Vectors with Enhanced Safety and Long-Term Gene Expression in Vivo," *Molecular Therapy* 5(6):731-738, Jun. 2002.
NCBI, GenBank accession No. CP000143.1, Oct. 7, 2005.
Yamagata "Roles of $O$-acetyl-$_L$-homoserine sulfhydrylases in micro-organisms," *Biochimie* 71:1125-1143 (1989).
UniProtKB Entry Q3J5D4—Comparing version 1 to 55, XP-002728470, http://www.uniprot.org/uniprot/Q3J5D4?version=1&version=55 (1 page) (Aug. 13, 2014).

* cited by examiner

O-ACETYLHOMOSERINE SULFHYDRYLASE OR MUTANT PROTEIN THEREOF, AND METHOD FOR CONVERTING TO METHIONINE USING THE SAME

STATEMENT REGARDING SEQUENCE LISTING

The Sequence Listing associated with this application is provided in text format in lieu of a paper copy, and is hereby incorporated by reference into the specification. The name of the text file containing the Sequence Listing is 200187_414USPC_SEQUENCE_LISTING.txt. The text file is 26.8 KB, was created on Jun. 20, 2013, and is being submitted electronically via EFS-Web.

TECHNICAL FIELD

The present invention relates to a novel protein having O-acetylhomoserine sulfhydrylase activity, a mutant protein thereof, a polynucleotide encoding the same, a recombinant vector comprising the polynucleotide, a microorganism transformed with the recombinant vector, and a method for producing methionine or acetic acid using the protein.

BACKGROUND ART

L-methionine which is one of the essential amino acids in vivo is contained in most of proteins and is present in a free state in soy sauce which is one of seasoning. It is widely used as feed and food additives, and is also used as infusion solution for medical usage or raw material for synthesizing medicines. Methionine is an important amino acid involved in methyl transfer reaction in vivo. First, by reacting with ATP, methionine is converted to δ-adenosylmethionine, which then donates methyl group to various acceptors; and then it is converted to cysteine via homocysteine and cystathionine. A red bread mold synthesizes methionine from cysteine. A scent of fermented foods such as soy sauce or cheese is often due to aldehyde, alcohol, and/or ester derived from methionine.

Also, methionine acts as a precursor of the compounds such as choline, lecithin, and creatine, and is used as raw material for synthesizing cysteine and taurine, and serving as a sulfur donor. In addition, methionine is associated with the synthesis of various neurotransmitters in the brain. Methionine and/or S-adenosyl-L-methionine (SAM) inhibit accumulation of fat in liver and arteries in vivo, and take various roles such as alleviating depression, inflammation, liver disease, and muscle pain. Furthermore, methionine and/or S-adenosyl-L-methionine provide various functions such as inhibiting fat deposition in a liver, which promotes fat metabolism, and arteries, increasing bloodstream circulation in a brain, heart, and kidney, stimulating digestion, promoting detoxification and excretion of toxic substances, and promoting the excretion of heavy metals such as lead. It has been reported that daily intake of 800 to 1,600 mg of methionine exhibits superior antidepressant effect, improvement of liver function in patients with liver diseases, particularly liver diseases caused by alcohol, excellent anti-inflammatory effect in bone joint disease, and stimulation of joint recovery in the same. Also, as an essential nutrient for hair, methionine is known to provide nourishment to the brittle hair, preventing hair loss.

For a chemical synthesis of methionine, most commonly L-methionine is produced through hydrolysis of 5-(β-methylmercaptoethyl)-hydantoin. However, when methionine is produced by such chemical synthesis process, there is disadvantage of producing mixed forms of L-type and D-type. In this regard, there is a patent disclosing the technique that allows a selective production of L-methionine using a biological approach (WO2008/013432). This method, named simply as a two-step method, comprises a process of converting the L-methionine precursor by fermentation and a process of converting the L-methionine precursor to L-methionine by using enzymes. The type of L-methionine precursor preferably comprises O-acetylhomoserine and O-succinylhomoserine. Development of the two-step method resolves all the existing problems such as toxicity of a substrate specific to sulfide, feedback control in a strain by methionine and SAM, and decomposition of intermediate product specific to cystathionine gamma synthase, O-succinylhomoserine sulfhydrylase, and O-acetylhomoserine sulfhydrylase. Furthermore, this method, which produces only L-methionine selectively, is superior to the conventional chemical synthesis process that produces both of D-methionine and L-methionine simultaneously, and this method can additionally produce organic acid, more specifically, succinic acid and acetic acid, as by-product through the same reaction.

The enzymatic conversion process in the two-step method employs the enzymes having cystathionine gamma synthase activity, O-succinylhomoserine sulfhydrylase activity or O-acetylhomoserine sulfhydrylase activity, and produces L-methionine and organic acids through enzyme reaction of O-acetylhomoserine or O-succinylhomoserine, which is a precursor of L-methionine, with methyl mercaptan.

In the enzymatic conversion reaction for producing L-methionine from O-acetylhomoserine, which is a precursor of L-methionine, various microbial-derived O-acetylhomoserine sulfhydrylases may be used. However, in order to be used as industrial convertase, the enzyme needs to meet several requirements to maximize cost-effectiveness. Firstly, the enzyme should have the characteristics of high activity and high conversion rate, and the overexpression thereof should be possible in *E. coli*. In general, for the reactions that use a purified enzyme, the activity of enzyme, reaction rate, and high affinity to a substrate are essential. But, if enzyme homogenate is added directly into the reaction, the overexpression of enzyme per unit cell should be possible in addition to having a high activity, in order to proceed the reaction with a minimal amount of homogenate. Secondly, the enzyme needs to maintain a high reaction rate with O-acetylhomoserine at high concentration, and the inhibition of its activity should be low even with accumulation of final products L-methionine and acetic acid to high concentration. Lastly, the enzyme should have a thermal stability to maintain its activity during the 1- to 5-hour long reaction. Considering the above requirements, a previously disclosed O-acetylhomoserine sulfhydrylase derived from *Hyphomonas neptunium* is an excellent enzyme, however in order to maximize the commercial value of the two-step method for producing methionine, a search for the enzymes with enhancement of the three characteristics is necessary.

DISCLOSURE

Technical Problem

The present inventors have obtained O-acetylhomoserine sulfhydrylase genes from various microbial sources and finally selected O-acetylhomoserine sulfhydrylase gene from *Rhodobacter sphaeroides* through experiments. Then after using the enzyme in a conversion reaction, the inventors have found that O-acetylhomoserine sulfhydrylase from *Rhodobacter sphaeroides* is an economically viable convertase to be applied in the two-step method for producing methionine, and also confirmed that the economic viability of the convertase can be enhanced by improving the enzyme through introducing mutations, thereby completing the present invention.

Technical Solution

One objective of the present invention is to provide a novel protein having O-acetylhomoserine sulfhydrylase activity.

Another objective of the present invention is to provide a polynucleotide encoding the novel protein.

Another objective of the present invention is to provide a mutant protein having enhanced O-acetylhomoserine sulfhydrylase activity.

Another objective of the present invention is to provide a polynucleotide encoding the mutant protein.

Another objective of the present invention is to provide a recombinant vector comprising the polynucleotide.

Another objective of the present invention is to provide a microorganism transformed with the recombinant vector.

Another objective of the present invention is to provide a method for producing methionine or acetic acid from the precursors O-acetylhomoserine and methyl mercaptan, using the protein, or microorganism producing the same.

Advantageous Effects

The present invention provides a protein having the activity of O-acetylhomoserine sulfhydrylase derived from *Rhodobacter sphaeroides*, which is required for producing L-methionine and acetic acid from a substrate methyl mercaptan ($CH_3SH$). If the protein is used, it has the advantage of producing L-methionine and acetic acid economically through having higher conversion rate and reduced reaction time compared to the existing methods that use a protein having the activity of O-acetylhomoserine sulfhydrylase from *Hyphomonas neptunium*. In addition, if the mutant protein with enhanced activity of O-acetylhomoserine sulfhydrylase of the present invention is used, this can minimize the amount of enzyme homogenate added, thereby easily producing L-methionine and acetic acid at high yield.

BEST MODE

Figure 1:
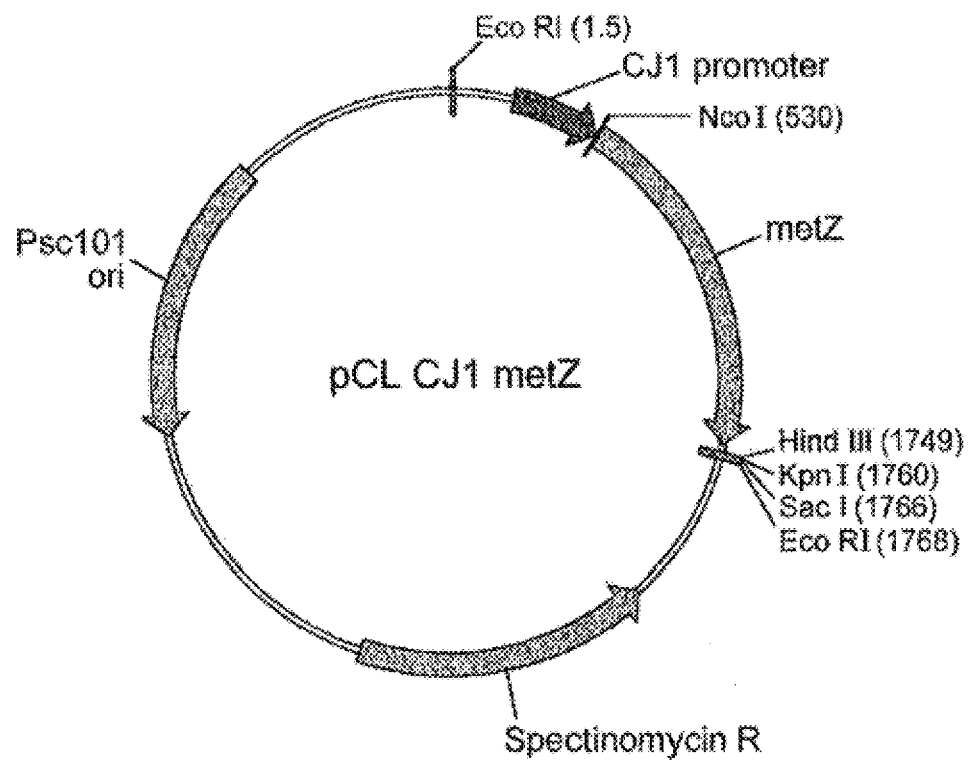
FIG. 1 represents the schematic diagram of pCL-$P_{CJ1}$-MetZhne vector.

As one aspect, the present invention provides a novel protein having O-acetylhomoserine sulfhydrylase activity.

In the present invention, the protein having O-acetylhomoserine sulfhydrylase activity refers to a novel protein capable of synthesizing L-methionine using O-acetylhomoserine, which is a precursor of L-methionine, and methyl mercaptan. The novel protein is preferably a protein having O-acetylhomoserine sulfhydrylase activity from *Rhodobacter sphaeroides*. For the purpose of the present invention, the novel protein includes any protein having O-acetylhomoserine sulfhydrylase activity without limitation, but it may preferably be the protein of SEQ ID No. 13.

As used herein, the term "O-acetylhomoserine" is a substance with a molecular weight of 161.16 and is the first specific intermediate in biosynthesis of methionine in microorganisms. In intestinal bacteria O-succinylhomoserine is used as an intermediate instead of O-acetylhomoserine, and in higher plants O-phosphohomoserine is used as an intermediate. O-acetylhomoserine is generated from L-homoserine and acetyl-CoA by homoserine acetyltransferase catalysis at the bifurcation with biosynthesis of threonine.

Patent Publication WO2008/013432 discloses a process of producing L-methionine using a two-step method, and in this process, O-succinylhomoserine and O-acetylhomoserine are the two types of O-acylhomoserine which is a precursor used for producing L-methionine.

As used herein, the term "precursor" refers to a substance produced at the preceding step of a final product in a metabolism or biosynthetic reaction. For the purpose of the present invention, the precursor refers to a metabolite produced by L-methionine precursor-producing strain as a part of the methionine-specific metabolic pathway, or derivatives thereof. Specifically, the L-methionine precursor of the present invention refers to O-succinylhomoserine or O-acetylhomoserine.

The enzymes capable of producing methionine from O-succinylhomoserine among the L-methionine precursors through enzyme conversion include cystathionine gamma synthase and O-succinylhomoserine sulfhydrylase. In general, the gene encoding cystathionine gamma synthase is commonly noted as metB, and the gene encoding O-succinylhomoserine sulfhydrylase is commonly noted as metZ. These enzymes have the following three activities.

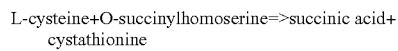

L-cysteine+O-succinylhomoserine=>succinic acid+ cystathionine

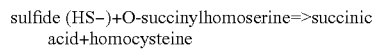

sulfide (HS−)+O-succinylhomoserine=>succinic acid+homocysteine

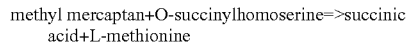

methyl mercaptan+O-succinylhomoserine=>succinic acid+L-methionine

O-acetylhomoserine sulfhydrylase is an enzyme capable of producing L-methionine by using O-acetylhomoserine which is another L-methionine precursor. In general, the gene encoding O-acetylhomoserine sulfhydrylase is commonly noted as metY. This enzyme has the following three activities.

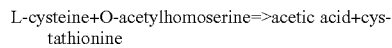

L-cysteine+O-acetylhomoserine=>acetic acid+cystathionine

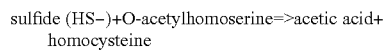

sulfide (HS−)+O-acetylhomoserine=>acetic acid+ homocysteine

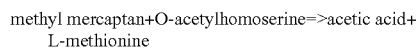

methyl mercaptan+O-acetylhomoserine=>acetic acid+ L-methionine

Using O-acetylhomoserine which requires less carbon sources such as glucose and raw sugar for producing two L-methionine precursors is more cost-effective in L-methionine production. However, while MetZ enzyme which is O-succinylhomoserine sulfhydrylase does not get a feedback inhibition from its final product L-methionine, MetY enzyme which is O-acetylhomoserine sulfhydrylase is inhibited by its product L-methionine, and therefore MetY is hard to use in enzymatic reaction.

In one example of the present invention, through testing various metZ genes for their activities, the *Rhodobacter sphaeroides*-derived metZ gene having O-acetylhomoserine sulfhydrylase activity was identified although it was previously expected to be an O-succinylhomoserine sulfhydrylase. Furthermore, it was confirmed that *Rhodobacter sphaeroides*-derived metZ does not get a feed inhibition by L-methionine. The selected protein having O-acetylhomoserine sulfhydrylase activity may have an amino acid sequence of SEQ ID No. 13.

In one example of the present invention, substrate specificity, expression level of convertase, and activity of convertase were compared among the proteins having the activity of O-acetylhomoserine sulfhydrylase derived from *Hyphomonas* species and O-acetylhomoserine sulfhydrylase derived from *Rhodobacter* species. As a result, it was found that when L-methionine is produced by using a mutant protein of O-acetylhomoserine sulfhydrylase derived from *Rhodobacter* species, the mutant protein showed higher substrate specificity toward O-acetylhomoserine than O-succinylhomoserine (Table 1), and it also demonstrated an improved enzymatic activity during early phase of reaction, improved reaction rate and L-methionine conversion rate (Table 2). In addition, when the inhibition levels by final products were compared among the recombinant mutant proteins derived from the two strains, O-acetylhomoserine sulfhydrylase derived from *Rhodobacter* species maintained a high activity in L-methionine production even with feedback inhibition by the final product thereof (Table 3). Furthermore, when a thermal stability of the enzyme relative to reaction temperature was compared, the mutant protein of O-acetylhomoserine sulfhydrylase derived from *Rhodobacter* species showed a superior thermal stability compared to the mutant protein of O-acetylhomoserine sulfhydrylase derived from *Hyphomonas* species (Table 4).

Therefore, the protein having O-acetylhomoserine sulfhydrylase activity of the present invention satisfies all the requirements to be used as industrial convertase including high activity, high conversion rate, overexpression in *E. coli*, low inhibition of enzyme activity by final product and capability to maintain thermal stability at the time of accumulation of final product, and thus by using the enzyme of the present invention, L-methionine and acetic acid can be produced at high rate and high efficiency.

As another aspect, the present invention provides a mutant protein having enhanced O-acetylhomoserine sulfhydrylase activity than a wild type.

As used herein, the term "mutation" or "mutant protein" refers to a culture or individual demonstrating a single stable genetic or non-genetic phenotypic change. In the present invention, a mutant protein preferably refers to a protein which activity is increased compared to the wild type due to a mutation in one or more of the genes encoding O-acetylhomoserine sulfhydrylase derived from *Rhodobacter sphaeroides*. The sequence of the mutant protein may comprise the sequence of protein having a homology of at least 80%, 90%, 95%, 96%, 97%, 98%, or 99% to the sequence of wild type. Preferably, the protein may be a mutant protein having an enhanced O-acetylhomoserine sulfhydrylase activity through a mutation wherein the $3^{rd}$ amino acid from the N-terminal of the protein represented by the amino acid sequence of SEQ ID No. 13 is substituted with an amino acid other than isoleucine, the $65^{th}$ amino acid from the same is substituted with an amino acid other than phenylalanine, and the $104^{th}$ amino acid from the same is substituted with an amino acid other than valine, or a combination of one or more of the three types of amino acid mutations is made. More preferably, two or more and even more preferably, three types of mutations can be combined. Even more preferably, the protein may be a mutant protein wherein the $3^{rd}$ amino acid from the N-terminal, isoleucine, is substituted with asparagine, and the $65^{th}$ amino acid, phenylalanine, is substituted with tyrosine, and the $104^{th}$ amino acid, valine, is substituted with alanine. The amino acid sequence of the mutant protein may preferably be a mutant protein having the amino acid sequence of SEQ ID No. 15, 16, 17, or 18.

Specifically, a mutant protein represented by the amino acid sequence of SEQ ID No. 15 is a variant form of the protein represented by the amino acid sequence of SEQ ID No. 13 wherein the $3^{rd}$ amino acid from the N-terminal of the same, isoleucine, is substituted with asparagine.

The mutant protein represented by the amino acid sequence of SEQ ID No. 16 has a substitution of phenylalanine, which is the $65^{th}$ amino acid from the N-terminal of the protein represented by the amino acid sequence of SEQ ID No. 13, by tyrosine.

The mutant protein represented by the amino acid sequence of SEQ ID No. 17 has a substitution of valine, which is the $104^{th}$ amino acid from the N-terminal of the protein represented by the amino acid sequence of SEQ ID No. 13, by alanine.

In addition, the mutant protein represented by the amino acid sequence of SEQ ID No. 18 has a substitution of isoleucine, which is the $3^{rd}$ amino acid from the N-terminal of the protein represented by the amino acid sequence of SEQ ID No. 13, by asparagine, a substitution of phenylalanine, the $65^{th}$ amino acid, by tyrosine, and a substitution of valine, the $104^{th}$ amino acid, by alanine.

In one example of the present invention, based on the above findings four mutant proteins such as I3N, F65Y, V104A and E182G with improved enzymatic activity of mutant protein of O-acetylhomoserine sulfhydrylase derived from *Rhodobacter* species were generated. Then, three valid mutant proteins such as I3N, F65Y, and V104A were selected by measuring the activity of the mutant proteins (Table 9). A vector comprising the combination of the three valid mutant proteins was prepared, and transfected into *E. coli*. After measuring the activity of each mutant protein, it was found that the mutant proteins had 1.75 times increased activity than that of wild type O-acetylhomoserine sulfhydrylase (Table 10).

As another aspect, the present invention provides a polynucleotide encoding a novel protein having O-acetylhomoserine sulfhydrylase activity or a mutant protein having enhanced O-acetylhomoserine sulfhydrylase activity than a wild type.

As used herein, the term "polynucleotide" refers to a polymer of nucleotides having nucleotide monomers linked in a long chain by covalent bonding, and generally it means a deoxyribonucleic acid (DNA) or ribonucleic acid (RNA) strand longer than a certain length. For the purpose of the present invention, the polynucleotide may be a polynucleotide fragment encoding the protein. This polynucleotide fragment comprises polynucleotide fragments having a homology of at least 80%, 90%, 95%, 96%, 97%, 98%, or 99% to the sequence of polynucleotide fragment having O-acetylhomoserine sulfhydrylase activity.

Preferably, the polynucleotide may be the polynucleotide represented by the nucleotide sequence of SEQ ID No. 14. The polynucleotide represented by the nucleotide sequence of SEQ ID No. 14 is the polynucleotide encoding the wild type protein having the amino acid sequence of SEQ ID No. 13.

In addition, the polynucleotide encoding the mutant protein may have the nucleotide sequence of SEQ ID No. 19, 20, 21 or 22. The polynucleotides having the nucleotide sequence of SEQ ID Nos. 19, 20, 21 and 22 are the polynucleotides encoding the proteins having the amino acid sequences of SEQ ID Nos. 15, 16, 17, and 18 respectively.

As used herein, the term "homology" refers to a percentage of identity between two polynucleotide moieties. Sequence correspondence from one moiety to another can be determined by the known technique in the art. For example, homology can be determined by aligning the sequence information of two polynucleotide molecules directly by using a computer program that is readily available and capable of aligning sequence information. In addition, homology can be determined by hybridizing the polynucleotides under the condition for forming a stable double-strand in the homologous regions and digesting the hybridized strand by a single-strand-specific nuclease to determine a size of digested fragment.

As used herein, the term "homologous" refers to the correlation between proteins where all grammatical forms and spelling variations include superfamily-derived proteins (e.g., immunoglobulin superfamily) and other species-derived homologous proteins (e.g., myosin light chain, etc.) having a 'common evolutionary origin'. Such proteins (and coding genes thereof) have a sequence homology reflected by a high degree of sequence similarity. However, in a general use and in the present invention, when the term "homogeny" is modified by an adjective such as 'very high', it refers to a sequence similarity, but not a common evolutionary origin.

As used herein, the term "sequence similarity" refers to the degree of identity or homology among the nucleotide sequences or amino acid sequences of the proteins which may or may not share a common evolutionary origin. In one specific example, when a polypeptide match between two amino acid sequences is least 21% for a fixed length of amino acid sequence (preferably at least about 50% and most preferably about 75%, 90%, 95%, 96%, 97% or 99%), those two sequences are 'substantially homologous' or 'substantially similar'. Substantially homologous sequences can be identified by comparing the sequences using standard software used in the data bank or, for example, by performing Southern hybridization experiment under the stringent conditions defined for a certain system. A defined condition suitable for hybridization is within the scope of conventional techniques in the art (for example, Sambrook et al., 1989, see infra).

As another aspect, the present invention provides a recombinant vector comprising a polynucleotide encoding the wild type O-acetylhomoserine sulfhydrylase or mutant protein thereof.

As used herein, the term "vector" refers to any carrier for cloning and/or transferring nucleotides to a host cell. A vector may be a replicon to allow for the replication of the fragments combined with other DNA fragments. "Replicon" refers to any genetic unit acting as a self-replicating unit for DNA replication in vivo, that is, replicable by the self-regulation (e.g., plasmid, phage, cosmid, chromosome, and virus). The vector may include viral and non-viral carrier for introducing nucleotides into a host cell in vitro, ex vivo or in vivo, and also may include a mini-spherical DNA. For example, the vector may be a plasmid without a bacterial DNA sequence. Removal of bacterial DNA sequences which are rich in CpG area has been conducted to reduce a silencing of the transgene expression and to promote more continuous expression from a plasmid DNA vector (Ehrhardt, A. et al. (2003) Hum Gene Ther 10: 215-25; Yet, N. S. (2002) Mol Ther 5: 731-38; Chen, Z. Y. et al. (2004) Gene Ther 11: 856-64). In addition, the vector may comprise a transposon such as Sleeping Beauty (Izsvak et al. J. Mol. Biol. 302:93-102 (2000)), or an artificial chromosome. Preferably, vectors such as pACYC177, pACYC184, pCL1920, pECCG117, pUC19, pBR322 and pMW118 can be used, and more preferably pCL_P$_{CJ1}$ which is pCL1920 vector inserted with CJ1 promoter (KR20060068505) can be used.

In the present invention, the polynucleotide may be operably linked to a recombinant vector. The term "operably linked" refers to the operable linking of a regulatory sequence for nucleotide expression with a nucleotide sequence encoding a target protein for performing its general function, thereby affecting the expression of a coding nucleotide sequence. Operable linking with a recombinant vector can be made by using a gene recombination technique known in the art, and a site-specific DNA cleavage and ligation can be done by using a restriction enzyme and ligase known in the art.

In addition, the recombinant vector may further comprise one or more antibiotic resistance genes selected from the group consisting of ampicillin resistance gene, kanamycin resistance gene, and chloramphenicol acetyl transferase gene.

As used herein, the term "antibiotic resistance gene" refers to a gene having resistance to antibiotics, and the cells comprising this gene survive even in the environment treated with the corresponding antibiotic. Therefore, the antibiotic resistance gene is effectively used as a selection marker for a large-scale production of plasmids in *E. coli*. In the present invention, as the antibiotic resistance gene is not a factor that significantly affects the expression efficiency which is obtained by an optimal combination of components of the vector which is the key feature of the present invention, any common antibiotic resistance gene can be used as a selection marker without limitation. Specifically, the resistance genes against ampicilin, tetracyclin, kanamycin, chloramphenicol, streptomycin, or neomycin can be used, and preferably spectinomycin resistance gene can be used.

As another aspect, the present invention provides a microorganism transformed with the recombinant vector, for producing O-acetylhomoserine sulfhydrylase.

As used herein, the term "transformation" refers to the introduction of genes into a host cell for the expression of the same. The method for transforming the vector of the present invention into the cells may include any method for introducing the nucleotides into the cells, and it can performed by selecting an appropriate standard technique known in the art. Method such as electroporation, calcium phosphate co-precipitation, retroviral infection, microinjection, DEAE-dextran and cationic liposome can be used, but is not limited thereto.

The transformed gene may be inserted into the chromosome of a host cell and located outside the chromosome, as long as it can be expressed in the host cell. In addition, the gene comprises DNA and RNA as a polynucleotide encoding polypeptide, and any gene that can be introduced and expressed in the host cell can be used without limitation. For example, the gene can be introduced into a host cell in a form of expression cassette which is a polynucleotide construct, comprising all the elements required for self-expression. The expression cassette usually comprises a promoter operably linked to the gene, transcription termination signal, ribosome binding sites, and translation termination signal. The expression cassette may be in a form of self-replicable expression vector. In addition, the gene may be the one introduced into a host cell by itself or in a form of polynucleotide construct and operably linked to the sequences required for the expression in the host cell.

As used herein, the term "microorganism transformed with recombinant vector" refers to the cell transfected with a vector comprising the gene encoding at least one target protein. In the present invention, if the microorganism comprises a wild type or mutant protein capable of producing O-acetylhomoserine sulfhydrylase through transformation of the recombinant vector, any of the prokaryotic and eukaryotic microorganisms can be used. For example, microbial strains belonging to *Escherichia* sp., *Erwinia* sp., *Serratia* sp., *Providencia* sp., *Corynebacteria* sp., *Pseudomonas* sp., *Leptospira* sp., *Salmonellar* sp., *Brevibacteria* sp., *Hypomononas* sp., *Chromobacterium* sp., and *Norcardia* sp. or fungi or yeast may be used. Preferably, microbial strain belonging to *Escherichia* sp., *Corynebacteria* sp., and *Leptospira* sp., and yeast, and more preferably microbial strain of *Escherichia* sp., and most preferably *E. coli* can be used.

As another aspect, the present invention provides a method for producing methionine or acetic acid, comprising adding the wild type protein, mutant protein, or microorganism producing the same to the mixture of O-acetylhomoserine and methyl mercaptan to thereby react the resulting mixture.

Figure 2A:
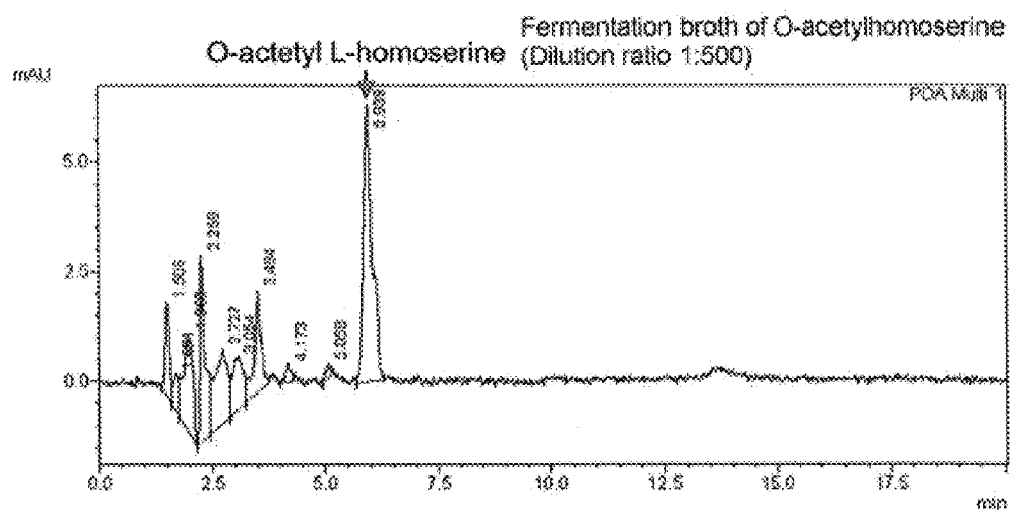
FIGS. 2a and 2b show the HPLC results, demonstrating the production of methionine. First, 5 to 10% homogenate of microorganism (of a total reaction volume) comprising the protein was added to the fermentation broth of O-acetylhomoserine, and the reaction was initiated by adding 15% Na-methyl mercaptan at a pH of 6 to 8. After 2 hours, the fermentation broth was collected and the cells were removed therefrom to analyze methionine production.
Figure 2B:
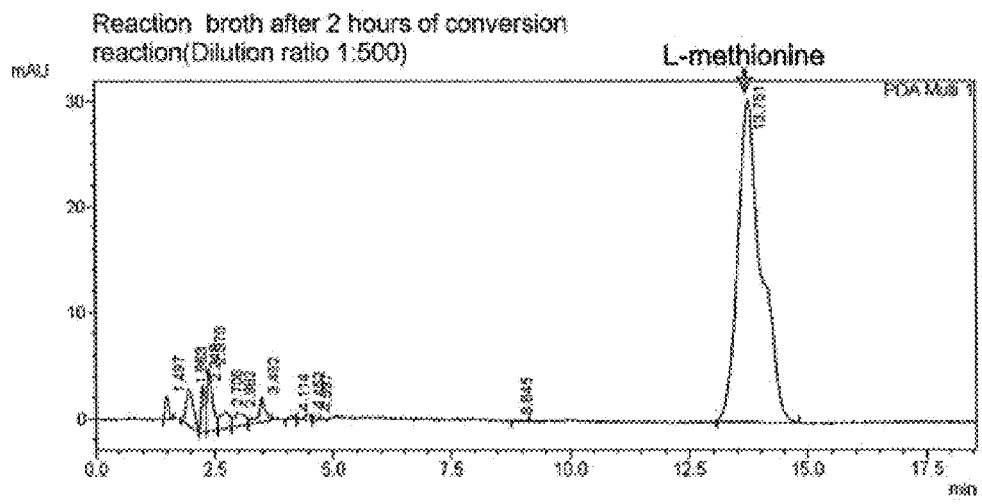

The O-acetylhomoserine refers to the purified form of O-acetylhomoserine or fermentation broth containing O-acetylhomoserine. Also, the methyl mercaptan refers to all of the following forms, a liquefied sodium methyl mercaptan ($CH_3S$—Na) form, and gaseous or liquefied methyl mercaptan ($CH_3SH$) form, as well as a methyl mercaptan comprising dimethylsulfide (DMS) which is disclosed in Patent Publication WO2010/098629. In one example of the present invention, for L-methionine conversion reaction, 5 to 10% homogenate of microorganisms (of a total reaction volume) comprising the polypeptide was added to the fermentation broth of O-acetylhomoserine, and the reaction was initiated by adding 15% Na-methyl mercaptan to the mixture at a pH of 6 to 8. Then, after 2 hours the fermentation broth was collected and the cells were removed therefrom, which was then analyzed by HPLC to identify methionine production. As shown in FIG. 2b, when the mutant protein of the present invention was used for producing methionine, the enzymatic conversion reaction and activity was superior to those in the existing producing strains. Also the reaction inhibition by the reaction product was minimized, and the thermal stability of the mutant protein was excellent, thereby suggesting that the mutant protein of the present invention can be effectively used for the industrial purpose.

As another aspect, the present invention provides a use of the protein as O-acetylhomoserine sulfhydrylase.

As described above, the protein of the present invention may be a wild type protein having the O-acetylhomoserine sulfhydrylase activity derived from *Rhodobacter sphaeroides* and a mutant protein thereof, and preferably it may be the protein having the amino acid sequence of SEQ ID Nos. 13 and 15 to 18. The protein of the present invention has high substrate specificity toward O-acetylhomoserine, thereby having the activity of O-acetylhomoserine sulfhydrylase or enhanced activity thereof, and therefore it can be used for producing methionine or acetic acid.

[Mode For Invention]

Hereinafter, the constitution and effect of present invention are described in more detail through providing Examples as below. However, these Examples are merely meant to illustrate the present invention, but in no way to limit, the scope of the present invention.

Example 1

Production of Methionine Convertase 1-1. O-acetylhomoserine Sulfhydrylase from *Hyphomonas* Species Primers were generated by obtaining the gene sequence of O-acetylhomoserine sulfhydrylase from *Hyphomonas neptunium* which converts O-acetylhomoserine to methionine from KEGG website (www.kegg.com). The chromosome of *Hyphomonas neptunium* was purchased from ATCC (USA). PCR reaction was performed with 30 cycles of denaturation step at 94° C. for 30 seconds, annealing step at 55° C. for 30 seconds, and extension step at 72° C. for 2 minutes, using the chromosome as a template and the primers of SEQ ID Nos. 1 and 2. HL PCR premix kit (Bioneer, Korea) was used for the PCR reaction.

DNA fragments obtained by the PCR reaction were cleaved by NcoI/HindIII and cloned into pCL-$P_{CJ1}$ vector digested with the same enzymes. The finally prepared vector was named as pCL-$P_{CJ1}$-MetZhne and the schematic diagram thereof was shown in FIG. 1. The cloned vectors were transformed into *Escherichia coli* K12 cells, and cultured in the LB medium plate added with 50 μg/L of spectinomycin, and the colony was selected. The selected colony was inoculated in 3 ml of LB medium containing 50 μg/L of spectinomycin, and cultured at 37° C., 200 rpm for 16 hours. The cell culture was re-inoculated in 25 ml of new LB liquid medium (in 250 ml flask), and cultured until O.D.$_{600}$ reaches 0.5 to 0.6 (for 2 to 3 hours) under the same culturing condition, and immediately after it was cultured in 500 ml of LB medium (in 1 L jar) added with 4% glucose until the depletion of glucose. The 1 ml of enzyme culture medium was collected, the supernatant was removed by centrifugation, and the pelleted cells were washed with 0.1M potassium phosphate buffer (pH 7.5). The cells were re-suspended in 1 mL of potassium phosphate buffer and crushed five times at 30-second intervals using ultrasound. The crushed cell homogenate was collected and a total amount of protein was quantified using the BIO-Rad protein quantification assay (BIO-Rad, USA). In addition, protein expression was confirmed by SDS-PAGE. Subsequently, the collected cell homogenate was used in the enzymatic conversion reaction.

1-2. O-acetylhomoserine Sulfhydrylase from *Rhodobacter* Species

The metZ gene encoding O-acetylhomoserine sulfhydrylase from *Rhodobacter sphaeroides* which converts O-acetylhomoserine to methionine was cloned in this experiment.

PCR reaction was performed with 30 cycles of denaturation step at 94° C. for 30 seconds, annealing step at 55° C. for 30 seconds, and extension step at 72° C. for 2 minutes, using the chromosome of *Rhodobacter sphaeroides* as a template and the primers of SEQ ID Nos. 3 and 4.

DNA fragments obtained from the PCR reaction were cleaved by NcoI/HindIII and cloned into pCL-$P_{CJ1}$ vector (Korea, CJ) digested with the same enzymes. Cell homogenate was obtained by using the cloned vectors in the same way as described in Example 1-1 and it was used in the enzymatic conversion reaction.

Example 2

Comparison of Convertase Expression Level, Substrate Specificity, ad Activity of Convertase The expression level and enzymatic activity were compared between O-acetylhomoserine sulfhydrylase derived from *Hyphomonas* species and O-acetylhomoserine sulfhydrylase derived from *Rhodobacter* species by using each of the cell homogenates obtained by the methods of Examples 1-1 and 1-2.

Figure 3:
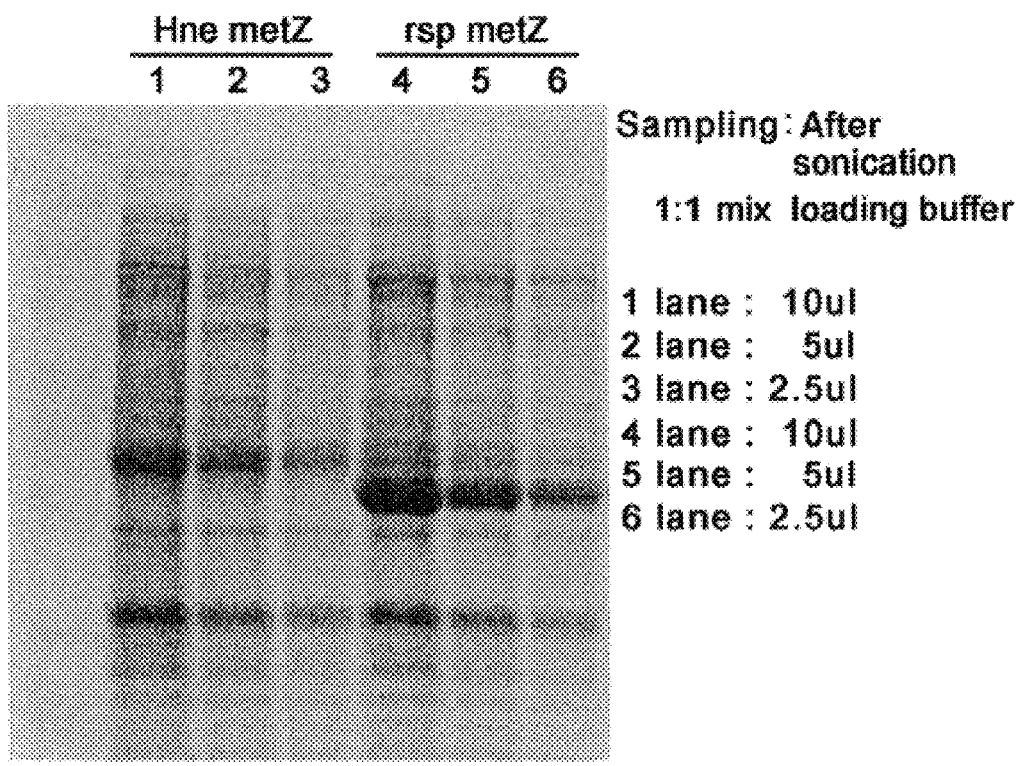
FIG. 3 shows the comparison of the expression level of convertase in 2.5 μl, 5 μl, 10 μl of the cell homogenate of O-acetylhomoserine sulfhydrylase from hyphomonas species (MetZ-hne) and O-acetylhomoserine sulfhydrylase from *rhodobacter* species (MetZ-rsp).

In general, the amount of protein is quantified by using a protein quantification assay from BIO-Rad, as mentioned in Example 1-1, however, when analyzing the mixture of protein with *E. coli* proteins such as enzyme homogenate, it is difficult to compare the expression level of certain enzymes using the protein quantification method. Therefore, in this experiment SDS-PAGE was used to compare the expression level of the convertase in the cell homogenate obtained from Examples 1-1 and 1-2. As a result of comparing O-acetylhomoserine sulfhydrylase derived from *Hyphomonas* species (Metz-hne) and O-acetylhomoserine sulfhydrylase derived from *Rhodobacter* species (MetZ-rsp) using 10 μl, 5 μl, and 2.5 μl of two cell homogenates, it was observed that MetZ-rsp showed about 4 times higher expression level than MetZ-hne (FIG. 3).

In order to determine substrate specificity of two enzymes, O-acylhomoserine was dissolved in 0.1M potassium phosphate buffer (pH 7.5) to a final concentration of 3 mM. In addition, pyridoxal 5'-phosphate (Sigma, USA), which is used as a cofactor, was added to the reaction mixture to a final concentration of 10 μM. Another substrate methyl mercaptan (Japan Tokyo Chemical Industry Ltd.) was added to the reaction mixture to a final concentration of 2 mM. The 1 ml of reaction mixture was put at 37° C., and then 10 μl of each enzyme extract was added to make a final protein concentration of 5 mg/ml. The progress of the reaction was confirmed by measuring the absorbance at 415 nm by collecting 100 μl of the reaction mixture after reaction started and adding it to 900 μl of 4 mg/ml DTNB solution (5,5-dithiobis(2-nitrobenzoic acid), Sigma, USA).

DTNB reacts with —SH group of methyl mercaptan remaining in the reaction mixture and synthesizes a yellow substance. Therefore, the progress of the reaction can be monitored by observing the disappearance of yellow colour in the reaction mixture as the methyl mercaptan in the reaction mixture is converted to methionine. Also, if the difference in DTNB absorbance before and after the reaction ($\Delta O.D._{415}$) is high, it suggests that the activity of enzyme is strong.

As a result of reaction O-acylhomoserine reaction mixture and enzyme solution, it was observed that both O-acetylhomoserine sulfhydrylase derived from *Hyphomonas neptunium* and O-acetylhomoserine sulfhydrylase derived from *Rhodobacter sphaeroides* showed higher substrate specificity toward O-acetylhomoserine than O-succinylhomoserine. The substrate specificity of each enzyme is shown simply as the number of '+' in Table 1. Overall, it was identified that both of the two strains have higher substrate specificity toward O-acetylhomoserine than O-succinylhomoserine.

TABLE 1

| Strain | Gene name | Substrate specificity | |
|---|---|---|---|
| | | O-succinylhomoserine (OSH) | O-acetylhomoserine (OAH) |
| *Hyphomonas Neptunium* | metZ | + | +++ |
| *Rhodobacter sphaeroides* | metZ | + | +++++ |

Example 3

Comparison of the MetZ-hne and MetZ-rsp Reactions During Early Phase in a Medium of O-acetylhomoserine at High Concentration In order to compare the conversion rates of MetZ-hne and MetZ-rsp enzymes in high concentration of O-acetylhomoserine, methionine conversion experiment was performed at O-acetylhomoserine concentration of 80 g/L. The relative methionine production rates were compared between O-acetylhomoserine sulfhydrylase derived from *Hyphomonas neptunium* and O-acetylhomoserine sulfhydrylase derived from *Rhodobacter sphaeroides* from the enzymatic conversion of 80 g/L O-acetylhomoserine in 1 ml tube scale over time. Reaction rates of O-acetylhomoserine sulfhydrylase can be compared by measuring the concentration of methionine produced from the reaction. More specifically, enzymatic conversion reaction was performed at 33° C. by adding 0.01 ml of sodium methyl mercaptan (15%, w/v) which is another substrate required for producing methionine, 0.01 ml of O-acetylhomoserine sulfhydrylase, and 0.1 mM pyridoxal 5'-phosphate the enzyme cofactor to 1 ml of 80 g/L O-acetylhomoserine, and stirring at 800 rpm. Each of the enzyme extracts was added to a final protein concentration of 5 mg/ml. The concentration of methionine and O-acetylhomoserine was analyzed by HPLC. The rate of methionine conversion was calculated as the number of moles of methionine produced from 1 mole of methyl mercaptan added into the reaction.

As shown in Table 2, O-acetylhomoserine sulfhydrylase derived from *Rhodobacter sphaeroides* showed higher reaction rate during early phase and higher conversion rate than O-acetylhomoserine sulfhydrylase derived from *Hyphomonas neptunium* even at high concentration of O-acetylhomoserine.

TABLE 2

| | | Time (in minutes) | | | | |
|---|---|---|---|---|---|---|
| | | 2 | 4 | 6 | 8 | 10 |
| MetZ-hne | Methionine (g/L) | 1.8 | 2.6 | 3.4 | 4.1 | 4.6 |
| | Conversion (%) | 25.71 | 37.14 | 48.57 | 58.57 | 65.71 |
| MetZ-rsp | Methionine (g/L) | 3.7 | 5.0 | 5.2 | 5.5 | 5.8 |
| | Conversion (%) | 52.4 | 71.0 | 73.3 | 78.1 | 81.9 |

Example 4

Comparison of the Degree of Reaction Inhibition by the Reaction Products Methionine and Acetic Acid In the two-step method, L-methionine and acetic acid are produced in the enzymatic reaction. However, it is known that a high concentration of L-methionine reduces the enzymatic reaction rate and acetic acid inhibits the enzyme activity through protein alteration.

For the enzymatic conversion of O-acetylhomoserine to L-methionine and acetic acid for industrial purpose, the enzyme should maintain high activity even with the above-described inhibition of enzyme activity. The activities of MetZ-hne and MetZ-rsp in the presence of L-methionine and acetic acid at high concentration were compared. Specifically, in the presence of 0.3M L-methionine (about 45 g/L) and 0.3M acetic acid, the activities were compared using a DTNB method described in Example 2. The 25 μl of 5 mg/ml cell homogenate was used in this reaction. The results showed that the residual activity of MetZ-hne and metZ-rsp were 42% and 50% respectively, and thus it was confirmed that Metz-rsp has a lower degree of enzyme activity inhibition even in the presence of L-methionine and acetic acid at high concentration (Table 3).

TABLE 3

|  |  | Time (minutes) | | ΔOD415 |
| --- | --- | --- | --- | --- |
|  |  | 0 | 1 |  |
| Met/Acetate 0M | MetZ-hne | 0.69 | 0.46 | 0.23 |
|  | MetZ-rsp | 0.69 | 0.48 | 0.21 |
| Met/Acetate 0.3M | MetZ-hne | 0.69 | 0.58 | 0.11 |
|  | MetZ-rsp | 0.69 | 0.60 | 0.09 |

In addition, the conversion reactions by two enzymes in the presence of 0.3M L-methionine and 0.3M acetic acid were analyzed, and the results are shown in Table 4.

TABLE 4

|  |  | Time (minutes) | | | |
| --- | --- | --- | --- | --- | --- |
|  |  | 0 | 5 | 10 | 15 |
| OD415 | MetZ-hne | 0.69 | 0.55 | 0.39 | 0.25 |
|  | MetZ-rsp | 0.69 | 0.49 | 0.31 | 0.12 |

Example 5

Comparison of Thermal Stability of MetZ-hne and MetZ-rsp Enzymes

In the enzymatic conversion process on an industrial scale, the reaction goes on for about 1 to 6 hours at a temperature of 33 to 37° C. In addition to a feedback inhibition by reaction products, the enzyme with low thermal stability has lower enzyme activity as the conversion reaction progresses. Thus, the thermal stability of enzyme is an important factor in industrial applicability and cost-effectiveness. In order to compare the thermal stability of the enzymes, each of the cell homogenates obtained by the methods of Examples 1-1 and 1-2 was heat-treated at 50° C. for 10, 30, 60, 120, and 240 minutes, and then the residual activity of enzymes was compared using a DTNB method of Example 2.

As shown in Table 5, O-acetylhomoserine sulfhydrylase derived from *Rhodobacter sphaeroides* showed the residual activity of 95% after 240 minute-long heat treatment at 45° C. compared to its activity prior to the heat treatment. On the other hand, MetZ-hne showed the residual activity of 75%, thereby suggesting that MetZ-rsp has a superior thermal stability.

TABLE 5

| 45° C. heat treatment | | Time (minutes) | | | | |
| --- | --- | --- | --- | --- | --- | --- |
|  |  | 0 | 10 | 30 | 60 | 120 | 240 |
| Relative activity (%) | MetZ-hne | 100 | 98 | 95 | 91 | 84 | 75 |
|  | MetZ-rsp | 100 | 100 | 100 | 99 | 97 | 95 |

Example 6

Enzymatic Conversion of O-acetylhomoserine Medium to L-methionine Using MetZ-rsp in a Batch Reactor In the present example, for evaluating the conversion activity of O-acetylhomoserine sulfhydrylase (metZ-rsp) identified in a tube scale now in a reactor system, a batch reactor having an optimal volume of 1 L was used. O-acetylhomoserine which is a substrate required for enzymatic conversion reaction was produced by fermenting a microbial strain disclosed in the prior art, and the cells were removed from the cultured fermentation broth using a centrifuge. The 500 mL of about 70 g/L culture medium was used (WO2008/013432). Since methyl mercaptan exists in a gaseous form at room temperature, the experiment was performed by using a sodium methyl mercaptan solution in a liquid form ($CH_3S$—Na, 4.7M, 33%, Arkema France) which was generated by adding methyl mercaptan to caustic soda solution. About 50 mL of sodium methyl mercaptan was used in enzymatic conversion reaction. As enzyme solution, 50 mL of MetZ-rsp cell homogenate produced by the method of Example 1 was added to the reaction along with 0.1 mM pyridoxal 5'-phosphate (Sigma, USA). The enzymatic conversion reaction was performed at a pH of 7.0 and at 33° C. with stirring at 700 rpm. The reaction was carried out for 3 hours while adding sodium methyl mercaptan. Concentrations of O-acetylhomoserine and L-methionine produced over the time were analyzed by HPLC and these results are shown in Table 6.

TABLE 6

| Time (minutes) | O-Acetylhomoserine (g/L) | L-Methionine (g/L) |
| --- | --- | --- |
| 0 | 66.1 | 0 |
| 30 | 20.6 | 34.1 |
| 90 | 9.5 | 42.0 |
| 120 | 3.1 | 47.2 |
| 180 | 0 | 49.5 |

Overall, it was observed that the enzymatic conversion reaction of O-acetylhomoserine medium to L-methionine using a MetZ-rsp enzyme solution in a 1 L batch reactor was fast and showed high conversion rate (97% mol conversion rate).

Example 7

Scale-up of the Enzymatic Conversion Reaction of O-acetylhomoserine Medium to L-methionine Using MetZ-rsp in a Batch Reactor In the present example, to evaluate the scale-up enzymatic conversion reaction system of methionine through the conversion activity of O-acetylhomoserine sulfhydrylase (metZ-rsp) identified in the 1 L batch reactor, methionine conversion reaction was performed using a 30 L batch reactor (Korea fermenter, Korea). O-acetylhomoserine which is a substrate required in enzymatic conversion reaction was produced, as in Example 6, by fermenting the microbial strains disclosed in prior art (WO2008/013432), and the microbial strain were removed from the cultured fermentation broth using a centrifuge. Supernatant was diluted by adding water to make the concentration of O-acetylhomoserine 66 g/L, and used in the reaction.

After 23 L of diluted fermentation supernatant was put in the fermenter, 500 ml of metZ-rsp enzyme homogenate generated by the method described in Example 1 was added to the same, and then a cofactor pyridoxal 5'-phosphate (Sigma, USA) was added to a final concentration of 0.1 mM. Subsequently, a pH of the reaction mixture was adjusted to 6.5 by adding ammonia gas and the temperature and stirring were set at 37° C. and at 300 rpm, respectively.

Methyl mercaptan (CH$_3$SH, 99.5%, UK, Intergas) in gaseous form was used, and it was put directly into the reaction mixture while controlling the amount of gas added using a mass flow controller. Since some of methyl mercaptan was evaporated in the reaction mixture and increased the pressure inside the reactor, the speed of supplying methyl mercaptan was adjusted to maintain the pressure to be less than 0.5 bar. About 220 L (470 g) of methyl mercaptan was added to the reaction for a total of 120 minutes while controlling the supplying speed to 3 to 5 L/min for the first 30 minutes of the fast reaction period and then to 1 to 2 L/min for the remaining 90 minutes of the slow reaction period. The total amount of methyl mercaptan added is the same molar amount as O-acetylhomoserine present in the reaction mixture during the enzymatic conversion reaction, all of which was consumed during synthesis of methionine. After completion of the reaction, the residual amount of methyl mercaptan was less than 0.1 g/L.

Since during the reaction, every time 1 mole of methionine is produced 1 mole of acetic acid is produced reducing the pH, a pH of the reaction was maintained to 6.5 by adding ammonia gas to raise the pH whenever it falls to 6.48. Reaction rate can be determined by measuring the slope of pH decrease, and the completion of reaction can be determined when pH decrease is slow.

The reaction was carried out for 6 hours while adding methyl mercaptan to the reaction. Changes in the concentrations of O-acetylhomoserine and L-methionine over time were analyzed by HPLC and the results are shown in FIG. 5.

Figure 4:
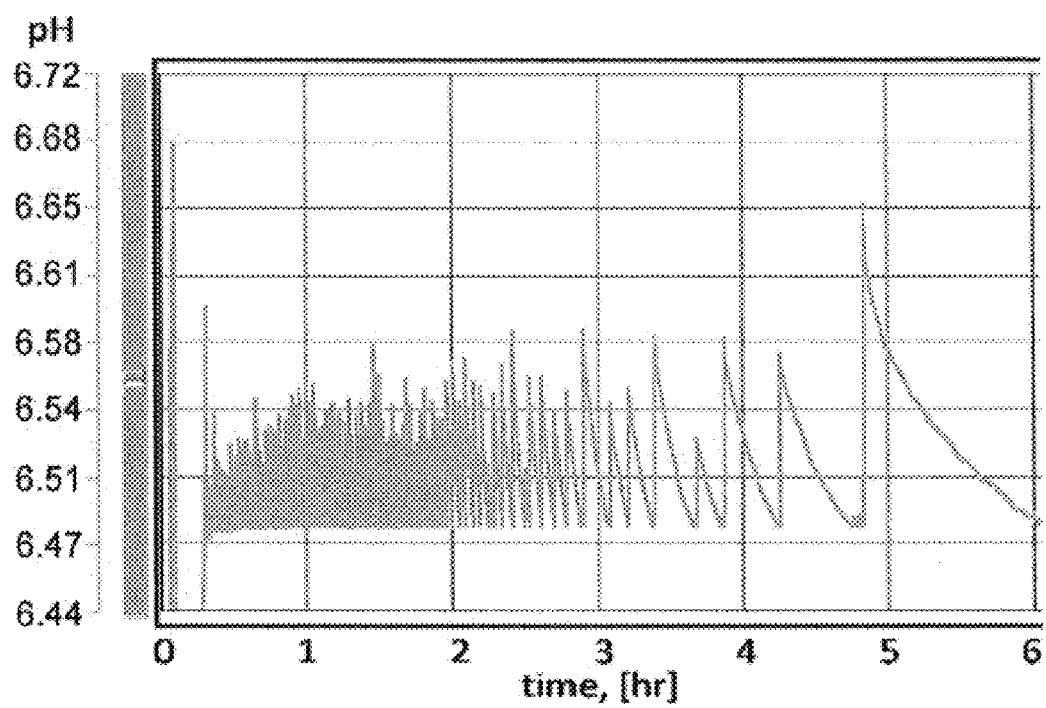
FIG. 4 demonstrates the pH changes during a conversion reaction in a 30 L batch reactor.
Figure 5:
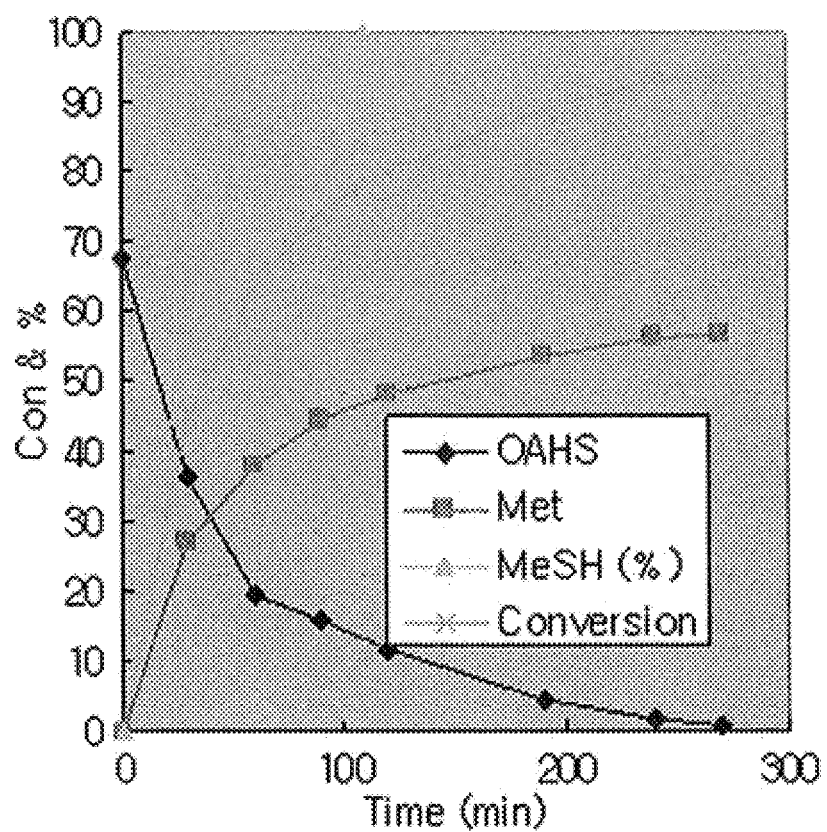
FIG. 5 shows the concentration changes of O-acetylhomoserine (OAHS) and L-methionine (Met) during a conversion reaction in a 30 L batch reactor, a ratio of methyl mercaptan (MeSH) added at each time setting a total amount of methyl mercaptan required as 100%, and a rate of methionine conversion at each time. The rate of methionine conversion is (g/g)% calculated by dividing a total amount of methionine produced up to each time point by a total amount of O-acetylhomoserine added (* rate of methionine conversion, 92.59%=rate of methionine conversion in mole, 100%).

The pH change profile during the reaction is shown in FIG. 4 and the graph of methionine conversion by the reaction is demonstrated in FIG. 5.

Overall, it was confirmed that even when gaseous methyl mercaptan was used in the enzymatic conversion reaction of O-acetylhomoserine medium to L-methionine using a metZ-rsp enzyme solution in a 30 L batch reactor, the methionine conversion with 98% molar conversion rate for 6 hours could be achieved.

Example 8

Improvement of Enzymatic Activity of metZ-rsp through Applying Mutation

In the present example, error-prone PCR was performed to induce random mutagenesis in a wild type metZ-rsp, and for this experiment a diversify PCR random mutagenesis kit (CLONTECH, USA) was used. In order to find the optimal conditions for establishing a target mutation rate, error-prone PCR was performed under the following two conditions at various concentrations of MnSO$_4$ and dGTP. The pCL-P$_{CJ1}$: metZ-rsp cloned in Example 1-2 was used as a DNA template where mutations are to be introduced.

TABLE 7

| | Condition 1 (µl) | Condition 2 (µl) |
|---|---|---|
| 10x Titaniun taq Buffer | 5 | 5 |
| MnSO$_4$ (8 mM) | 2 | 4 |
| dGTP (2 mM) | 1 | 2 |
| 50x dNTP Mix | 1 | 1 |
| Titanium Taq Polymerase | 1 | 1 |
| Forward primer | 2 | 2 |
| Reverse primer | 2 | 2 |
| Template DNA | 1 | 1 |
| dH$_2$0 | 35 | 32 |
| Total | 50 | 50 |
| Error-prone PCR condition | 94° C.: 30 seconds | |
| Error-prone PCR condition | 25 cycles 94° C.: 30 seconds 55° C.: 30 seconds 68° C.: 60 seconds | |
| Error-prone PCR condition | 68° C.: 60 seconds | |

The products of error-prone PCR performed under the conditions of Table 7 were cleaved with NcoI/HindIII, and cloned into pCL-P$_{CJ1}$ vector which was digested with the same enzymes. The cloned mutant library was transformed into Escherichia coli K12 cells, which were then cultured in a LB medium plate containing 50 µg/L pectinomycin. After culturing, 50 colonies were selected, and then sequencing analysis was performed to determine the mutation rate and check the occurrence of mutation at various locations. Sequencing analysis results demonstrated that the mutation rate was 2.4 kb$^{-1}$ under Condition 1, and 2.9 kb$^{-1}$ under Condition 2. Based on these results, it was determined that both of Conditions 1 and 2 could yield a suitable mutation rate for generating a mutant library, and thus screening of valid mutations was performed using the libraries produced under the above conditions.

The resulting cells were cultured in a first 96 deep-well plate, and treated with BugBuster solution in 1:1 ratio (MERCK, USA) to obtain cell homogenate. Then, 50 µl of the cell homogenate was collected and mixed with 50 µl of reaction mixture comprising 300 mM O-acetylhomoserine and 1 mM substrate of L-cysteine. The resulting reaction mixture was reacted for 60 minutes at a room temperature while adding 50 uL of DTNB solution at designated times. The O.D. values were measured at 415 nm after color formation and the results are shown in Table 8.

TABLE 8

| | Time (minutes) | | | | | |
|---|---|---|---|---|---|---|
| | 0 | 5 | 10 | 15 | 30 | 60 |
| OD415 | 2.17 | 1.19 | 0.65 | 0.50 | 0.37 | 0.30 |
| Compensated OD | 2.01 | 1.00 | 0.40 | 0.23 | 0.05 | 0.00 |
| Background Signal, 415 nm | 0.16 | 0.19 | 0.25 | 0.27 | 0.32 | 0.30 |

In the plot of DTNB color level over time, the O.D. values of residual L-cysteine are 1.19 and 0.65 at 5 minutes and 10 minutes after the reaction, respectively. In the actual screening, the mutants with less than 1.0 DTNB color level of residual cysteine after 5 minutes of enzymatic reaction were selected.

Candidate mutants that showed significantly increased activity were selected using the above screening method. Subsequently, nucleotide sequence alignment was performed to screen the valid mutation in the candidate mutants. Then finally the mutants comprising 4 types of mutations such as I3N (SEQ ID NO: 15), F65Y (SEQ ID NO: 16), V104A (SEQ ID NO: 17) and E182G were selected. Finally selected mutations were to be introduced as a candidate mutation, and by introducing each type of candidate mutations individually to a pCL-P$_{CJ1}$:metZ-rsp standard vector, the increased activity was validated. To generate the vectors introduced with each type of candidate mutations, the metZ-rsp expression vector introduced with each candidate mutation was produced using the primers of SEQ ID Nos. 5 and 6 for I3N mutation, the primers of SEQ ID Nos. 7 and 8 for F65Y mutation, the primers of SEQ ID Nos. 9 and 10 for 104A mutation, and the primers of SEQ ID Nos. 11 and 12 for E182G mutation. Successful introduction of mutation was confirmed by sequencing analysis (Macrogen, Korea). The generated mutant vector was transformed into *E. coli* K12, and cultured in a LB medium flask at 33° C. and 200 rpm for 15 hours. Then the cultured samples were analyzed to validate each candidate mutation. Results are shown in Table 9.

TABLE 9

| Mutation | OD562 nm | Activity | Unit | Spec. activity | Spec. unit |
|---|---|---|---|---|---|
| Wild type | 9.18 | 1.63 | 32.67 | 0.18 | 3.56 |
| I3N | 8.93 | 1.89 | 37.73 | 0.21 | 4.22 |
| F65Y | 8.83 | 2.00 | 39.93 | 0.23 | 4.52 |
| V104A | 8.60 | 1.88 | 37.67 | 0.22 | 4.38 |
| E182G | 9.53 | 1.43 | 28.60 | 0.15 | 3.00 |

The flask evaluation after introducing each candidate mutation demonstrated that I3N (SEQ ID No. 15), F65Y (SEQ ID No. 16), and V104A (SEQ ID No. 17) are the valid mutation showing increased activity compared to the existing control group of metZ-rsp. On the other hand, E182G mutation was determined to be invalid for having increased activity, and thus it was excluded for the subsequent experiment.

All of the three types of valid mutations including I3N, F65Y and V104A that were confirmed to have increased activity were introduced into the vector pCL-P$_{CJ1}$:metZ-rsp vector (named as pCL-P$_{CJ1}$:metZ-rspM3) to generate a vector with even more enhanced activity. Three types of mutations were introduced one by one into the vector using the above-listed primers. The prepared expression vector with three types of mutations was transformed into *E. coli* K12 and cultured in a flask. Then the cell culture was analyzed to evaluate the activity of the expression vector and the results are shown in Table 10.

TABLE 10

| Mutation | Activity | Spec. activity |
|---|---|---|
| pCL-P$_{CJ1}$:metZ-rsp | 1.00 | 1.00 |
| pCL-P$_{CJ1}$:metZ-rspM3 | 1.75 | 1.73 |

As shown in Table 10, it was confirmed that the pCL-P$_{CJ1}$:metZ-rsp M3 with three types of valid mutations introduced have 1.75 times increased activity than the pCL-P$_{CJ1}$:metZ-rsp.

The invention claimed is:

1. A mutant protein of a polypeptide of SEQ ID No. 13 having O-acetylhomoserine sulfhydrylase activity, wherein said mutant protein has all of SEQ ID No. 13 except for one or more substitution selected from the group consisting of substitution of the isoleucine at position 3 with an amino acid other than isoleucine, substitution of the phenylalanine at position 65 with tyrosine, and substitution of the valine at position 104 with an amino acid other than valine.

2. The mutant protein according to claim 1, wherein the mutation is made by substitution of the 3$^{rd}$ amino acid from the N-terminal with asparagine, and substitution of the 104$^{th}$ amino acid with alanine.

3. The mutant protein according to claim 1, having the amino acid sequence selected from the group consisting of SEQ ID Nos. 15 to 18.

4. A polynucleotide encoding the mutant protein of claim 1.

5. The polynucleotide according to claim 4 having the nucleotide sequence selected from the group consisting of SEQ ID Nos. 19 to 22.

6. A recombinant vector comprising the polynucleotide of claim 4.

7. A microorganism transformed with the recombinant vector of claim 6 for producing O-acetylhomoserine sulfhydrylase.

8. The microorganism according to claim 7, which is *Escherichia coli* (*E. coli*).

9. A method for producing methionine or acetic acid, comprising adding a protein having O-acetylhomoserine sulfhydrylase activity and comprising the amino acid sequence of SEQ ID No. 13 or a microorganism producing the same to a mixture of O-acetylhomoserine and methyl mercaptan to thereby react the resulting mixture.

10. A recombinant vector comprising the polynucleotide of claim 5.

11. A method for producing methionine or acetic acid, comprising adding a protein of claim 1 or a microorganism producing the same to a mixture of O-acetylhomoserine and methyl mercaptan to thereby react the resulting mixture.

12. A method for producing methionine or acetic acid, comprising adding a protein of claim 3 or a microorganism producing the same to a mixture of O-acetylhomoserine and methyl mercaptan to thereby react the resulting mixture.

* * * * *

SEQUENCE LISTING

```
<160> NUMBER OF SEQ ID NOS: 22

<210> SEQ ID NO 1
<211> LENGTH: 23
<212> TYPE: DNA
<213> ORGANISM: Artificial Sequence
<220> FEATURE:
<223> OTHER INFORMATION: primer for neptunium chromosome

<400> SEQUENCE: 1
aattccatgg cggatgcacc cgg                                           23

<210> SEQ ID NO 2
<211> LENGTH: 30
<212> TYPE: DNA
<213> ORGANISM: Artificial Sequence
<220> FEATURE:
<223> OTHER INFORMATION: primer for Hyphomonas neptunium

<400> SEQUENCE: 2
aattaagctt tcacaagctg ttaagcgaag                                    30

<210> SEQ ID NO 3
<211> LENGTH: 26
<212> TYPE: DNA
<213> ORGANISM: Artificial Sequence
<220> FEATURE:
<223> OTHER INFORMATION: primer for Rhodobacter sphaeroides chromosome

<400> SEQUENCE: 3
aattccatgg gtatcgcgtt tcgtga                                        26
```

```
<210> SEQ ID NO 4
<211> LENGTH: 28
<212> TYPE: DNA
<213> ORGANISM: Artificial Sequence
<220> FEATURE:
<223> OTHER INFORMATION: primer for Rhodobacter sphaeroides chromosome

<400> SEQUENCE: 4
aattaagctt tcagatcacc gcgagcgc                                    28

<210> SEQ ID NO 5
<211> LENGTH: 44
<212> TYPE: DNA
<213> ORGANISM: Artificial Sequence
<220> FEATURE:
<223> OTHER INFORMATION: primer for I3N mutants

<400> SEQUENCE: 5
aaaaggagat ataccatggg taacgcgttt cgtgaaggac ggac                  44

<210> SEQ ID NO 6
<211> LENGTH: 44
<212> TYPE: DNA
<213> ORGANISM: Artificial Sequence
<220> FEATURE:
<223> OTHER INFORMATION: primer for I3N mutants

<400> SEQUENCE: 6
gtccgtcctt cacgaaacgc gttacccatg gtatatctcc tttt                  44

<210> SEQ ID NO 7
<211> LENGTH: 44
<212> TYPE: DNA
<213> ORGANISM: Artificial Sequence
<220> FEATURE:
<223> OTHER INFORMATION: primer for F65Y mutants

<400> SEQUENCE: 7
catcgagacc ggcgccgacg aatacatcta tgcccgctac ggca                  44

<210> SEQ ID NO 8
<211> LENGTH: 44
<212> TYPE: DNA
<213> ORGANISM: Artificial Sequence
<220> FEATURE:
<223> OTHER INFORMATION: primer for F65Y mutants

<400> SEQUENCE: 8
tgccgtagcg ggcatagatg tattcgtcgg cgccggtctc gatg                  44

<210> SEQ ID NO 9
<211> LENGTH: 44
<212> TYPE: DNA
<213> ORGANISM: Artificial Sequence
<220> FEATURE:
<223> OTHER INFORMATION: primer for V104A mutants

<400> SEQUENCE: 9
ggcatggccg cgatccacgg cgcgctcacc tcgatcgtgc gggc                  44

<210> SEQ ID NO 10
<211> LENGTH: 44
<212> TYPE: DNA
<213> ORGANISM: Artificial Sequence
<220> FEATURE:
<223> OTHER INFORMATION: primer for V104A mutants
```

<400> SEQUENCE: 10
gcccgcacga tcgaggtgag cgcgccgtgg atcgcggcca tgcc    44

<210> SEQ ID NO 11
<211> LENGTH: 44
<212> TYPE: DNA
<213> ORGANISM: Artificial Sequence
<220> FEATURE:
<223> OTHER INFORMATION: primer for E182G mutants

<400> SEQUENCE: 11
gccgatatcg gcgccatcgc cggcatcgcc catgccgtgg gcgc    44

<210> SEQ ID NO 12
<211> LENGTH: 44
<212> TYPE: DNA
<213> ORGANISM: Artificial Sequence
<220> FEATURE:
<223> OTHER INFORMATION: primer for E182G mutants

<400> SEQUENCE: 12
gcgcccacgg catgggcgat gccggcgatg gcgccgatat cggc    44

<210> SEQ ID NO 13
<211> LENGTH: 404
<212> TYPE: PRT
<213> ORGANISM: Artificial Sequence
<220> FEATURE:
<223> OTHER INFORMATION: metZ-rsp amino acid sequence

<400> SEQUENCE: 13

```
Met Gly Ile Ala Phe Arg Glu Gly Arg Thr Gly Met Thr Lys Asp Trp
 1               5                  10                  15

Lys Thr Arg Thr Gln Leu Val His Gly Gly Ser Arg Ser Gln Tyr
            20                  25                  30

Gly Glu Met Ala Glu Ala Ile Phe Leu Thr Gln Gly Phe Val Tyr Asp
        35                  40                  45

Ser Ala Glu Gln Ala Glu Ala Arg Phe Ile Glu Thr Gly Ala Asp Glu
    50                  55                  60

Phe Ile Tyr Ala Arg Tyr Gly Asn Pro Thr Thr Arg Met Phe Glu Glu
65                  70                  75                  80

Arg Ile Ala Ala Val Glu Gly Thr Glu Asp Ala Phe Ala Thr Ala Ser
                85                  90                  95

Gly Met Ala Ala Ile His Gly Val Leu Thr Ser Ile Val Arg Ala Gly
            100                 105                 110

Asp His Leu Val Ala Ala Arg Ala Leu Phe Gly Ser Cys Ile Tyr Ile
        115                 120                 125

Leu Glu Glu Val Leu Gly Arg Phe Gly Val Glu Val Thr Phe Val Asp
    130                 135                 140

Gly Thr Asp Leu Asp Gln Trp Arg Ala Ala Val Arg Pro Gly Thr Lys
145                 150                 155                 160

Ala Val Phe Phe Glu Ser Val Ser Asn Pro Thr Leu Glu Val Ala Asp
                165                 170                 175

Ile Gly Ala Ile Ala Glu Ile Ala His Ala Val Gly Ala Leu Val Ile
            180                 185                 190

Val Asp Asn Val Phe Ala Thr Pro Val Phe Ser Thr Ala Val Arg Gln
        195                 200                 205

Gly Ala Asp Val Val Ile Tyr Ser Ala Thr Lys His Ile Asp Gly Gln
    210                 215                 220
```

Gly Arg Ala Leu Gly Gly Val Val Cys Ala Ser Gln Ala Phe Ile Arg
225                 230                 235                 240

Lys Val Leu Glu Pro Phe Met Lys His Thr Gly Gly Ser Met Ser Pro
            245                 250                 255

Phe Asn Ala Trp Leu Met Leu Asn Gly Met Ala Thr Leu Asp Leu Arg
        260                 265                 270

Cys Arg Ala Met Ala Asp Thr Ala Glu Lys Ile Ala Arg Ala Leu Glu
    275                 280                 285

Gly His Pro Gln Leu Gly Arg Val Ile His Pro Ala Leu Glu Ser His
290                 295                 300

Pro Gln His Glu Met Ala Lys Ala Gln Met Glu Arg Pro Gly Thr Met
305                 310                 315                 320

Ile Ala Leu Asp Leu Ala Gly Gly Lys Glu Ala Ala Phe Arg Phe Leu
                325                 330                 335

Asp Ala Leu Arg Ile Val Lys Ile Ser Asn Asn Leu Gly Asp Ala Arg
            340                 345                 350

Ser Ile Ala Thr His Pro Ala Thr Thr His Gln Arg Leu Ser Asp
        355                 360                 365

Ala Gln Lys Ala His Leu Gly Ile Thr Pro Gly Leu Val Arg Leu Ser
370                 375                 380

Val Gly Leu Glu Asp Ala Asp Asp Leu Ile Ala Asp Leu Lys Gln Ala
385                 390                 395                 400

Leu Ala Val Ile

<210> SEQ ID NO 14
<211> LENGTH: 1215
<212> TYPE: DNA
<213> ORGANISM: Artificial Sequence
<220> FEATURE:
<223> OTHER INFORMATION: metZ-rsp nucleotide sequence

<400> SEQUENCE: 14

```
atgggtatcg cgtttcgtga aggacggacg ggcatgacga aggactggaa gacaaggacg      60
caactcgtcc acggggcag ccgccggagc cagtatggcg aaatggccga ggcgatcttc     120
ctgacccagg gcttcgtcta cgactcggcc gcacaggccg aagcgcgctt catcgagacc     180
ggcgccgacg aattcatcta tgcccgctac ggcaaccccca cgacgcgcat gttcgaagag     240
cgcatcgcgg ccgtcgaggg caccgaggat gcgttcgcca ccgcctcggg catggccgcg     300
atccacggcg tgctcaccct gatcgtgcgg gcgggcgatc atctggtggc ggcgcgcgct     360
ctgttcggct cctgcatcta catcctcgag gaggtgctgg gccgattcgg cgtcgaggtg     420
accttcgtcg acggcaccga tctcgatcag tggcgcgcgg cggtgcggcc cggcacgaag     480
gccgtgttct tcgagtcggt ctcgaatccg acgctcgagg tggccgatat cggcgccatc     540
gccgagatcg cccatgccgt gggcgcgctc gtcatcgtgg acaatgtctt cgcgacgccc     600
gtcttctcga cggcggtgcg gcagggcgcg gatgtggtga tctattcggc caccaagcac     660
atcgacgggc aagggcgcgc gctcggcggc gtggtctgcg cctcgcaggc cttcatccgc     720
aaggtgctcg aacccttcat gaagcacacc ggcggctcga tgagcccctt caacgcctgg     780
ctcatgctga acgggatggc gacgctcgac ctgcgctgcc gcgcgatggc cgacacggcc     840
gagaagatcg cccgcgcgct cgagggccat ccgcagctcg gccgcgtgat ccatcccgcg     900
ctggaaagcc acccgcagca cgagatggcc aaggcgcaga tggagcgtcc cggcacgatg     960
atcgcgctcg acctcgccgg gggcaaggag gcggccttcc gcttcctcga cgccctgagg    1020
```

```
atcgtgaaga tctccaacaa tctgggcgat gcccgctcga tcgcgaccca cccggcaacg   1080
accacccacc agcgtctttc cgacgcgcag aaggcccatc tcggcatcac gcccgggctc   1140
gtgcggctgt cggtggggct cgaggatgcg gacgacctga tcgccgatct gaaacaggcg   1200
ctcgcggtga tctga                                                    1215
```

<210> SEQ ID NO 15
<211> LENGTH: 404
<212> TYPE: PRT
<213> ORGANISM: Artificial Sequence
<220> FEATURE:
<223> OTHER INFORMATION: metZ-rsp I3N amino acid sequence

<400> SEQUENCE: 15

```
Met Gly Asn Ala Phe Arg Glu Gly Arg Thr Gly Met Thr Lys Asp Trp
1               5                   10                  15

Lys Thr Arg Thr Gln Leu Val His Gly Gly Ser Arg Ser Gln Tyr
            20                  25                  30

Gly Glu Met Ala Glu Ala Ile Phe Leu Thr Gln Gly Phe Val Tyr Asp
        35                  40                  45

Ser Ala Glu Gln Ala Glu Ala Arg Phe Ile Glu Thr Gly Ala Asp Glu
    50                  55                  60

Phe Ile Tyr Ala Arg Tyr Gly Asn Pro Thr Thr Arg Met Phe Glu Glu
65                  70                  75                  80

Arg Ile Ala Ala Val Glu Gly Thr Glu Asp Ala Phe Ala Thr Ala Ser
                85                  90                  95

Gly Met Ala Ala Ile His Gly Val Leu Thr Ser Ile Val Arg Ala Gly
            100                 105                 110

Asp His Leu Val Ala Ala Arg Ala Leu Phe Gly Ser Cys Ile Tyr Ile
        115                 120                 125

Leu Glu Glu Val Leu Gly Arg Phe Gly Val Glu Val Thr Phe Val Asp
    130                 135                 140

Gly Thr Asp Leu Asp Gln Trp Arg Ala Ala Val Arg Pro Gly Thr Lys
145                 150                 155                 160

Ala Val Phe Phe Glu Ser Val Ser Asn Pro Thr Leu Glu Val Ala Asp
                165                 170                 175

Ile Gly Ala Ile Ala Glu Ile Ala His Ala Val Gly Ala Leu Val Ile
            180                 185                 190

Val Asp Asn Val Phe Ala Thr Pro Val Phe Ser Thr Ala Val Arg Gln
        195                 200                 205

Gly Ala Asp Val Val Ile Tyr Ser Ala Thr Lys His Ile Asp Gly Gln
    210                 215                 220

Gly Arg Ala Leu Gly Gly Val Val Cys Ala Ser Gln Ala Phe Ile Arg
225                 230                 235                 240

Lys Val Leu Glu Pro Phe Met Lys His Thr Gly Gly Ser Met Ser Pro
                245                 250                 255

Phe Asn Ala Trp Leu Met Leu Asn Gly Met Ala Thr Leu Asp Leu Arg
            260                 265                 270

Cys Arg Ala Met Ala Asp Thr Ala Glu Lys Ile Ala Arg Ala Leu Glu
        275                 280                 285

Gly His Pro Gln Leu Gly Arg Val Ile His Pro Ala Leu Glu Ser His
    290                 295                 300

Pro Gln His Glu Met Ala Lys Ala Gln Met Glu Arg Pro Gly Thr Met
305                 310                 315                 320
```

```
Ile Ala Leu Asp Leu Ala Gly Gly Lys Glu Ala Phe Arg Phe Leu
            325                 330                 335

Asp Ala Leu Arg Ile Val Lys Ile Ser Asn Asn Leu Gly Asp Ala Arg
        340                 345                 350

Ser Ile Ala Thr His Pro Ala Thr Thr Thr His Gln Arg Leu Ser Asp
        355                 360                 365

Ala Gln Lys Ala His Leu Gly Ile Thr Pro Gly Leu Val Arg Leu Ser
        370                 375                 380

Val Gly Leu Glu Asp Ala Asp Asp Leu Ile Ala Asp Leu Lys Gln Ala
385                 390                 395                 400

Leu Ala Val Ile

<210> SEQ ID NO 16
<211> LENGTH: 404
<212> TYPE: PRT
<213> ORGANISM: Artificial Sequence
<220> FEATURE:
<223> OTHER INFORMATION: metZ-rsp F65Y amino acid sequence

<400> SEQUENCE: 16

Met Gly Ile Ala Phe Arg Glu Gly Arg Thr Gly Met Thr Lys Asp Trp
1               5                   10                  15

Lys Thr Arg Thr Gln Leu Val His Gly Gly Ser Arg Ser Gln Tyr
            20                  25                  30

Gly Glu Met Ala Glu Ala Ile Phe Leu Thr Gln Gly Phe Val Tyr Asp
        35                  40                  45

Ser Ala Glu Gln Ala Glu Ala Arg Phe Ile Glu Thr Gly Ala Asp Glu
    50                  55                  60

Tyr Ile Tyr Ala Arg Tyr Gly Asn Pro Thr Thr Arg Met Phe Glu Glu
65                  70                  75                  80

Arg Ile Ala Ala Val Glu Gly Thr Glu Asp Ala Phe Ala Thr Ala Ser
                85                  90                  95

Gly Met Ala Ala Ile His Gly Val Leu Thr Ser Ile Val Arg Ala Gly
            100                 105                 110

Asp His Leu Val Ala Ala Arg Ala Leu Phe Gly Ser Cys Ile Tyr Ile
        115                 120                 125

Leu Glu Glu Val Leu Gly Arg Phe Gly Val Glu Val Thr Phe Val Asp
    130                 135                 140

Gly Thr Asp Leu Asp Gln Trp Arg Ala Ala Val Arg Pro Gly Thr Lys
145                 150                 155                 160

Ala Val Phe Phe Glu Ser Val Ser Asn Pro Thr Leu Glu Val Ala Asp
                165                 170                 175

Ile Gly Ala Ile Ala Glu Ile Ala His Ala Val Gly Ala Leu Val Ile
            180                 185                 190

Val Asp Asn Val Phe Ala Thr Pro Val Phe Ser Thr Ala Val Arg Gln
        195                 200                 205

Gly Ala Asp Val Val Ile Tyr Ser Ala Thr Lys His Ile Asp Gly Gln
    210                 215                 220

Gly Arg Ala Leu Gly Gly Val Cys Ala Ser Gln Ala Phe Ile Arg
225                 230                 235                 240

Lys Val Leu Glu Pro Phe Met Lys His Thr Gly Gly Ser Met Ser Pro
                245                 250                 255

Phe Asn Ala Trp Leu Met Leu Asn Gly Met Ala Thr Leu Asp Leu Arg
            260                 265                 270
```

```
Cys Arg Ala Met Ala Asp Thr Ala Glu Lys Ile Ala Arg Ala Leu Glu
            275                 280                 285

Gly His Pro Gln Leu Gly Arg Val Ile His Pro Ala Leu Glu Ser His
    290                 295                 300

Pro Gln His Glu Met Ala Lys Ala Gln Met Glu Arg Pro Gly Thr Met
305                 310                 315                 320

Ile Ala Leu Asp Leu Ala Gly Gly Lys Glu Ala Ala Phe Arg Phe Leu
                325                 330                 335

Asp Ala Leu Arg Ile Val Lys Ile Ser Asn Asn Leu Gly Asp Ala Arg
            340                 345                 350

Ser Ile Ala Thr His Pro Ala Thr Thr Thr His Gln Arg Leu Ser Asp
        355                 360                 365

Ala Gln Lys Ala His Leu Gly Ile Thr Pro Gly Leu Val Arg Leu Ser
    370                 375                 380

Val Gly Leu Glu Asp Ala Asp Asp Leu Ile Ala Asp Leu Lys Gln Ala
385                 390                 395                 400

Leu Ala Val Ile
```

<210> SEQ ID NO 17
<211> LENGTH: 404
<212> TYPE: PRT
<213> ORGANISM: Artificial Sequence
<220> FEATURE:
<223> OTHER INFORMATION: metZ-rsp V104A amino acid sequence

<400> SEQUENCE: 17

```
Met Gly Ile Ala Phe Arg Glu Gly Arg Thr Gly Met Thr Lys Asp Trp
1               5                   10                  15

Lys Thr Arg Thr Gln Leu Val His Gly Gly Ser Arg Ser Gln Tyr
            20                  25                  30

Gly Glu Met Ala Glu Ala Ile Phe Leu Thr Gln Gly Phe Val Tyr Asp
        35                  40                  45

Ser Ala Glu Gln Ala Glu Ala Arg Phe Ile Glu Thr Gly Ala Asp Glu
    50                  55                  60

Phe Ile Tyr Ala Arg Tyr Gly Asn Pro Thr Thr Arg Met Phe Glu Glu
65                  70                  75                  80

Arg Ile Ala Ala Val Glu Gly Thr Glu Asp Ala Phe Ala Thr Ala Ser
                85                  90                  95

Gly Met Ala Ala Ile His Gly Ala Leu Thr Ser Ile Val Arg Ala Gly
            100                 105                 110

Asp His Leu Val Ala Ala Arg Ala Leu Phe Gly Ser Cys Ile Tyr Ile
        115                 120                 125

Leu Glu Glu Val Leu Gly Arg Phe Gly Val Glu Val Thr Phe Val Asp
    130                 135                 140

Gly Thr Asp Leu Asp Gln Trp Arg Ala Ala Val Arg Pro Gly Thr Lys
145                 150                 155                 160

Ala Val Phe Phe Glu Ser Val Ser Asn Pro Thr Leu Glu Val Ala Asp
                165                 170                 175

Ile Gly Ala Ile Ala Glu Ile Ala His Ala Val Gly Ala Leu Val Ile
            180                 185                 190

Val Asp Asn Val Phe Ala Thr Pro Val Phe Ser Thr Ala Val Arg Gln
        195                 200                 205

Gly Ala Asp Val Val Ile Tyr Ser Ala Thr Lys His Ile Asp Gly Gln
    210                 215                 220
```

```
Gly Arg Ala Leu Gly Gly Val Val Cys Ala Ser Gln Ala Phe Ile Arg
225                 230                 235                 240

Lys Val Leu Glu Pro Phe Met Lys His Thr Gly Gly Ser Met Ser Pro
            245                 250                 255

Phe Asn Ala Trp Leu Met Leu Asn Gly Met Ala Thr Leu Asp Leu Arg
        260                 265                 270

Cys Arg Ala Met Ala Asp Thr Ala Glu Lys Ile Ala Arg Ala Leu Glu
    275                 280                 285

Gly His Pro Gln Leu Gly Arg Val Ile His Pro Ala Leu Glu Ser His
290                 295                 300

Pro Gln His Glu Met Ala Lys Ala Gln Met Glu Arg Pro Gly Thr Met
305                 310                 315                 320

Ile Ala Leu Asp Leu Ala Gly Gly Lys Glu Ala Ala Phe Arg Phe Leu
                325                 330                 335

Asp Ala Leu Arg Ile Val Lys Ile Ser Asn Asn Leu Gly Asp Ala Arg
            340                 345                 350

Ser Ile Ala Thr His Pro Ala Thr Thr Thr His Gln Arg Leu Ser Asp
        355                 360                 365

Ala Gln Lys Ala His Leu Gly Ile Thr Pro Gly Leu Val Arg Leu Ser
370                 375                 380

Val Gly Leu Glu Asp Ala Asp Asp Leu Ile Ala Asp Leu Lys Gln Ala
385                 390                 395                 400

Leu Ala Val Ile

<210> SEQ ID NO 18
<211> LENGTH: 404
<212> TYPE: PRT
<213> ORGANISM: Artificial Sequence
<220> FEATURE:
<223> OTHER INFORMATION: metZ-rsp I3N F65Y V104A amino acid sequence

<400> SEQUENCE: 18

Met Gly Asn Ala Phe Arg Glu Gly Arg Thr Gly Met Thr Lys Asp Trp
1               5                   10                  15

Lys Thr Arg Thr Gln Leu Val His Gly Gly Ser Arg Arg Ser Gln Tyr
            20                  25                  30

Gly Glu Met Ala Glu Ala Ile Phe Leu Thr Gln Gly Phe Val Tyr Asp
        35                  40                  45

Ser Ala Glu Gln Ala Glu Ala Arg Phe Ile Glu Thr Gly Ala Asp Glu
    50                  55                  60

Tyr Ile Tyr Ala Arg Tyr Gly Asn Pro Thr Thr Arg Met Phe Glu Glu
65                  70                  75                  80

Arg Ile Ala Ala Val Glu Gly Thr Glu Asp Ala Phe Ala Thr Ala Ser
                85                  90                  95

Gly Met Ala Ala Ile His Gly Ala Leu Thr Ser Ile Val Arg Ala Gly
            100                 105                 110

Asp His Leu Val Ala Ala Arg Ala Leu Phe Gly Ser Cys Ile Tyr Ile
        115                 120                 125

Leu Glu Glu Val Leu Gly Arg Phe Gly Val Glu Val Thr Phe Val Asp
    130                 135                 140

Gly Thr Asp Leu Asp Gln Trp Arg Ala Ala Val Arg Pro Gly Thr Lys
145                 150                 155                 160

Ala Val Phe Phe Glu Ser Val Ser Asn Pro Thr Leu Glu Val Ala Asp
                165                 170                 175
```

```
Ile Gly Ala Ile Ala Glu Ile Ala His Ala Val Gly Ala Leu Val Ile
                180                 185                 190

Val Asp Asn Val Phe Ala Thr Pro Val Phe Ser Thr Ala Val Arg Gln
            195                 200                 205

Gly Ala Asp Val Val Ile Tyr Ser Ala Thr Lys His Ile Asp Gly Gln
        210                 215                 220

Gly Arg Ala Leu Gly Gly Val Val Cys Ala Ser Gln Ala Phe Ile Arg
225                 230                 235                 240

Lys Val Leu Glu Pro Phe Met Lys His Thr Gly Ser Met Ser Pro
                245                 250                 255

Phe Asn Ala Trp Leu Met Leu Asn Gly Met Ala Thr Leu Asp Leu Arg
            260                 265                 270

Cys Arg Ala Met Ala Asp Thr Ala Glu Lys Ile Ala Arg Ala Leu Glu
        275                 280                 285

Gly His Pro Gln Leu Gly Arg Val Ile His Pro Ala Leu Glu Ser His
        290                 295                 300

Pro Gln His Glu Met Ala Lys Ala Gln Met Glu Arg Pro Gly Thr Met
305                 310                 315                 320

Ile Ala Leu Asp Leu Ala Gly Gly Lys Glu Ala Ala Phe Arg Phe Leu
                325                 330                 335

Asp Ala Leu Arg Ile Val Lys Ile Ser Asn Asn Leu Gly Asp Ala Arg
            340                 345                 350

Ser Ile Ala Thr His Pro Ala Thr Thr Thr His Gln Arg Leu Ser Asp
        355                 360                 365

Ala Gln Lys Ala His Leu Gly Ile Thr Pro Gly Leu Val Arg Leu Ser
        370                 375                 380

Val Gly Leu Glu Asp Ala Asp Asp Leu Ile Ala Asp Leu Lys Gln Ala
385                 390                 395                 400

Leu Ala Val Ile

<210> SEQ ID NO 19
<211> LENGTH: 1215
<212> TYPE: DNA
<213> ORGANISM: Artificial Sequence
<220> FEATURE:
<223> OTHER INFORMATION: metZ-rsp I3N nucleotide sequence

<400> SEQUENCE: 19
atgggtaacg cgtttcgtga aggacggacg ggcatgacga aggactggaa gacaaggacg      60
caactcgtcc acggggggcag ccgccggagc cagtatggcg aaatggccga ggcgatcttc    120
ctgacccagg gcttcgtcta cgactcggcc gcacaggccg aagcgcgctt catcgagacc    180
ggcgccgacg aattcatcta tgcccgctac ggcaacccca cgacgcgcat gttcgaagag    240
cgcatcgcgg ccgtcgaggg caccgaggat gcgttcgcca ccgcctcggg catggccgcg    300
atccacggcg tgctcacctc gatcgtgcgg gcgggcgatc atctggtggc ggcgcgcgct    360
ctgttcggct cctgcatcta catcctcgag gaggtgctgg ccgattcgg cgtcgaggtg    420 accttcgtcg acggcaccga tctcgatcag tggcgcgcgg cggtgcggcc cggcacgaag    480
gccgtgttct tcgagtcggt ctcgaatccg acgctcgagg tggccgatat cggcgccatc    540
gccgagatcg cccatgccgt gggcgcgctc gtcatcgtgg acaatgtctt cgcgacgccc    600
gtcttctcga cggcggtgcg gcagggcgcg gatgtggtga tctattcggc caccaagcac    660
atcgacgggc aaggggcgcg gctcggcggc gtggtctgcg cctcgcaggc cttcatccgc    720
aaggtgctcg aacccttcat gaagcacacc ggcggctcga tgagcccctt caacgcctgg    780
```

```
ctcatgctga acgggatggc gacgctcgac ctgcgctgcc gcgcgatggc cgacacggcc      840
gagaagatcg cccgcgcgct cgagggccat ccgcagctcg gccgcgtgat ccatcccgcg      900
ctggaaagcc acccgcagca cgagatggcc aaggcgcaga tggagcgtcc cggcacgatg      960
atcgcgctcg acctcgccgg gggcaaggag gcggccttcc gcttcctcga cgccctgagg      1020
atcgtgaaga tctccaacaa tctgggcgat gcccgctcga tcgcgaccca cccggcaacg      1080
accacccacc agcgtctttc cgacgcgcag aaggcccatc tcggcatcac gcccgggctc      1140
gtgcggctgt cggtggggct cgaggatgcg gacgacctga tcgccgatct gaaacaggcg      1200
ctcgcggtga tctga                                                      1215
```

<210> SEQ ID NO 20
<211> LENGTH: 1215
<212> TYPE: DNA
<213> ORGANISM: Artificial Sequence
<220> FEATURE:
<223> OTHER INFORMATION: metZ-rsp F65Y nucleotide sequence

<400> SEQUENCE: 20

```
atgggtatcg cgtttcgtga aggacggacg ggcatgacga aggactggaa gacaaggacg      60
caactcgtcc acgggggcag ccgccggagc cagtatggcg aaatggccga ggcgatcttc      120
ctgacccagg gcttcgtcta cgactcggcc gcacaggcca agcgcgcgctt catcgagacc      180 ggcgccgacg aatacatcta tgcccgctac ggcaacccca cgacgcgcat gttcgaagag      240
cgcatcgcgg ccgtcgaggg caccgaggat gcgttcgcca ccgcctcggg catggccgcg      300
atccacggcg tgctcacctc gatcgtgcgg gcgggcgatc atctggtggc ggcgcgcgct      360
ctgttcggct cctgcatcta catcctcgag gaggtgctgg gccgattcgg cgtcgaggtg      420
accttcgtcg acggcaccga tctcgatcag tggcgcgcgg cggtgcggcc cggcacgaag      480
gccgtgttct tcgagtcggt ctcgaatccg acgctcgagg tggccgatat cggcgccatc      540
gccgagatcg cccatgccgt gggcgcgctc gtcatcgtgg acaatgtctt cgcgacgccc      600
gtcttctcga cggcggtgcg gcagggcgcg gatgtggtga tctattcggc caccaagcac      660
atcgacgggc aagggcgcgc gctcggcggc gtggtctgcg cctcgcaggc cttcatccgc      720
aaggtgctcg aacccttcat gaagcacacc ggcggctcga tgagcccctt caacgcctgg      780
ctcatgctga acgggatggc gacgctcgac ctgcgctgcc gcgcgatggc cgacacggcc      840
gagaagatcg cccgcgcgct cgagggccat ccgcagctcg gccgcgtgat ccatcccgcg      900
ctggaaagcc acccgcagca cgagatggcc aaggcgcaga tggagcgtcc cggcacgatg      960
atcgcgctcg acctcgccgg gggcaaggag gcggccttcc gcttcctcga cgccctgagg      1020
atcgtgaaga tctccaacaa tctgggcgat gcccgctcga tcgcgaccca cccggcaacg      1080
accacccacc agcgtctttc cgacgcgcag aaggcccatc tcggcatcac gcccgggctc      1140
gtgcggctgt cggtggggct cgaggatgcg gacgacctga tcgccgatct gaaacaggcg      1200
ctcgcggtga tctga                                                      1215
```

<210> SEQ ID NO 21
<211> LENGTH: 1215
<212> TYPE: DNA
<213> ORGANISM: Artificial Sequence
<220> FEATURE:
<223> OTHER INFORMATION: metZ-rsp V104A nucleotide sequence

<400> SEQUENCE: 21

```
atgggtatcg cgtttcgtga aggacggacg ggcatgacga aggactggaa gacaaggacg      60
caactcgtcc acgggggcag ccgccggagc cagtatggcg aaatggccga ggcgatcttc     120
ctgacccagg gcttcgtcta cgactcggcc gcacaggccg aagcgcgctt catcgagacc     180
ggcgccgacg aattcatcta tgcccgctac ggcaaccccca cgacgcgcat gttcgaagag    240
cgcatcgcgg ccgtcgaggg caccgaggat gcgttcgcca ccgcctcggg catggccgcg    300
atccacggcg cgctcaccte gatcgtgcgg gcgggcgatc atctggtggc ggcgcgcgct    360
ctgttcggct cctgcatcta catcctcgag gaggtgctgg gccgattcgg cgtcgaggtg    420
accttcgtcg acggcaccga tctcgatcag tggcgcgcgg cggtgcggcc cggcacgaag    480
gccgtgttct tcgagtcggt ctcgaatccg acgctcgagg tggccgatat cggcgccatc    540
gccgagatcg cccatgccgt gggcgcgctc gtcatcgtgg acaatgtctt cgcgacgccc    600
gtcttctcga cggcggtgcg gcagggcgcg gatgtggtga tctattcggc caccaagcac    660
atcgacgggc aagggcgcgc gctcggcggc gtggtctgcg cctcgcaggc cttcatccgc    720
aaggtgctcg aacccttcat gaagcacacc ggcggctcga tgagccccttcaacgcctgg    780
ctcatgctga cgggatggc gacgctcgac ctgcgctgcc gcgcgatggc cgacacggcc    840
gagaagatcg cccgcgcgct cgagggccat ccgcagctcg gccgcgtgat ccatcccgcg    900
ctggaaagcc acccgcagca cgagatggcc aaggcgcaga tggagcgtcc cggcacgatg    960
atcgcgctcg acctcgccgg gggcaaggag gcggccttcc gcttcctcga cgccctgagg   1020
atcgtgaaga tctccaacaa tctgggcgat gcccgctcga tcgcgaccca ccggcaacg    1080
accacccacc agcgtctttc cgacgcgcag aaggcccatc tcggcatcac gcccgggctc   1140
gtgcggctgt cggtggggct cgaggatgcg gacgacctga tcgccgatct gaaacaggcg   1200
ctcgcggtga tctga                                                     1215
```

<210> SEQ ID NO 22
<211> LENGTH: 1215
<212> TYPE: DNA
<213> ORGANISM: Artificial Sequence
<220> FEATURE:
<223> OTHER INFORMATION: metZ-rsp I3N F65Y V104A nucleotide sequence

<400> SEQUENCE: 22

```
atgggtaacg cgtttcgtga aggacggacg ggcatgacga aggactggaa gacaaggacg     60
caactcgtcc acgggggcag ccgccggagc cagtatggcg aaatggccga ggcgatcttc    120
ctgacccagg gcttcgtcta cgactcggcc gcacaggccg aagcgcgctt catcgagacc    180
ggcgccgacg aatacatcta tgcccgctac ggcaaccccca cgacgcgcat gttcgaagag   240
cgcatcgcgg ccgtcgaggg caccgaggat gcgttcgcca ccgcctcggg catggccgcg   300
atccacggcg cgctcaccte gatcgtgcgg gcgggcgatc atctggtggc ggcgcgcgct   360
ctgttcggct cctgcatcta catcctcgag gaggtgctgg gccgattcgg cgtcgaggtg   420
accttcgtcg acggcaccga tctcgatcag tggcgcgcgg cggtgcggcc cggcacgaag   480
gccgtgttct tcgagtcggt ctcgaatccg acgctcgagg tggccgatat cggcgccatc   540
gccgagatcg cccatgccgt gggcgcgctc gtcatcgtgg acaatgtctt cgcgacgccc   600
gtcttctcga cggcggtgcg gcagggcgcg gatgtggtga tctattcggc caccaagcac   660
atcgacgggc aagggcgcgc gctcggcggc gtggtctgcg cctcgcaggc cttcatccgc   720
aaggtgctcg aacccttcat gaagcacacc ggcggctcga tgagccccttcaacgcctgg   780
```

```
ctcatgctga  acgggatggc  gacgctcgac  ctgcgctgcc  gcgcgatggc  cgacacggcc    840
gagaagatcg  cccgcgcgct  cgagggccat  ccgcagctcg  gccgcgtgat  ccatcccgcg    900
ctggaaagcc  acccgcagca  cgagatggcc  aaggcgcaga  tggagcgtcc  cggcacgatg    960
atcgcgctcg  acctcgccgg  gggcaaggag  gcggccttcc  gcttcctcga  cgccctgagg   1020
atcgtgaaga  tctccaacaa  tctgggcgat  gcccgctcga  tcgcgaccca  cccggcaacg   1080
accacccacc  agcgtctttc  cgacgcgcag  aaggcccatc  tcggcatcac  gcccgggctc   1140
gtgcggctgt  cggtggggct  cgaggatgcg  gacgacctga  tcgccgatct  gaaacaggcg   1200
ctcgcggtga  tctga                                                       1215
```